US006426403B1

(12) United States Patent
Nakata et al.

(10) Patent No.: US 6,426,403 B1
(45) Date of Patent: Jul. 30, 2002

(54) TRAF FAMILY MOLECULES, POLYNUCLEOTIDES ENCODING THEM, AND ANTIBODIES AGAINST THEM

(75) Inventors: Motomi Nakata, Yokohama; Hiroyasu Nakano; Hideo Yagita, both of Tokyo; Ko Okumura, 9-2-610, Azusawa 3-chome, Itabashi-ku, Tokyo 174-0051, all of (JP)

(73) Assignee: Ko Okumura, Tokyo (JP)

( * ) Notice: Subject to any disclaimer, the term of this patent is extended or adjusted under 35 U.S.C. 154(b) by 0 days.

(21) Appl. No.: 09/138,277

(22) Filed: Aug. 18, 1998

Related U.S. Application Data

(63) Continuation-in-part of application No. PCT/JP97/00512, filed on Feb. 24, 1997.

(30) Foreign Application Priority Data

Feb. 22, 1996 (JP) .............................................. 8-034674

(51) Int. Cl.[7] .................... C07K 14/52; C07H 21/04; C12N 15/00
(52) U.S. Cl. ..................... 530/350; 530/351; 435/69.1; 536/23.1
(58) Field of Search .................... 530/300, 350, 530/351; 435/183, 174, 69.1; 536/23.1

(56) References Cited

PUBLICATIONS

Cell, vol. 78, No. 34, Aug. 26, 1994, "Duplications in Mouse Forelimb", pp. 681–692.
"Proceedings of the National Academy of Sciencies of the United States of America", Sep. 3, 1996, vol. 93, No. 18, pp. 9437–9442.
"TRAF5, an Activtor of NF–kB and Putative Signal Transducer for the Lymphotoxin–B Receptor", The Journal of Biological Chemistry, Jun. 21, 1996, vol. 271, No. 25, pp. 14661–14664.
"Human TNF Receptor–Associated Factor 5 (TRAF5): cDNA Cloning, Expression and Assignment of the TRAF5 Gene to Chromosome 1q32", Genomics 42, 26–32 (1997).
"A Novel Ring Finger Protein Interacts with the Cytoplasmic Domain of CD40*", The Journal of Biological Chemistry, vol. 269, No. 48, pp. 30069–30072 (Dec. 1994).
"A novel member of the TRAF famly of putative signal transducing proteins binds to the cytosolic domain of CD40", Sato et al., FEBS Letters 358 (1995) 113–118.
"The TNF Receptor 1–Associated Protein TRADD Signals Cell Death and NF–kB Activation", Cell, vol. 81, 495–504, May 19, 1995.
"Involvement of CRAF1, a Relative of TRAF, in CD40 Signaling", Cheng, et al., Science, vol. 267, Mar. 10, 1995, pp. 1494–1498.
TRAF2–Mediated Activation of NF–kB by TNF Receptor 2 and CD40, Rothe et al., Science, vol. 269, Sep. 8, 1995, pp. 1424–1427.
"CD30/TNF receptor–associated factor interaction: NF–kB activation and binding specificity", Lee at al., Proc. Natl. Acad. Sci. USA 93 (1996) pp. 96999703.

*Primary Examiner*—Sean McGarry
*Assistant Examiner*—Janet Epps
(74) *Attorney, Agent, or Firm*—McDermott, Will & Emery

(57) ABSTRACT

This invention relates to a TRAF family molecule, a polynucleotide encoding the molecules, an antibody against the molecules, and an antisense polynucleotide of the molecule. Employing an oligo-DNA primer capable of amplifying the most highly conserved region of a known TRAF family molecule, PCR was performed with the aid of cDNA derived from various cell strains and tissues as a template. Thus, the base sequence of the gene of an unknown TRAF family molecule and the amino acid sequence of the TRAF family molecule encoded by the gene were elucidated. An antibody against the molecule was also prepared. By utilizing the TRAF family molecules, genes thereof, and antibodies against the molecules, there are provided methods for elucidating the functions of the proteins and methods for elucidating the signal transduction system of the TNF-R family involving the molecules, as well as probes for research and diagosis, which suggest applications in therapeutic agents.

2 Claims, 11 Drawing Sheets

Fig.6A

5' CGGAATTC TAY YTN AAY GGN GAY GG 3'
   ‾‾‾‾‾‾‾‾
   EcoRI SITE

Fig.6B

5' CGGAATTC ADR AAN ATN GYR TCR TC 3'
   ‾‾‾‾‾‾‾‾
   EcoRI SITE

Fig.11

```
hTRAF5    1:MAYSEEHKGMPCGFIRQNSISLDFEPSIEYQFVERLEERYKCAFCHSVLHNPHQTGC   60
mTRAF5    1:--H--QAAV--A----------------DT------Q--------------------   60 hTRAF5   61:GHRFCQHCILSLRELNTVPICPVDKEVIKSQEVFKDNCCKREVLNLYVYCSNAPGCNAKV  120
mTRAF5   61:------Q--R------S--------------P--------H---K-------RI--   120 hTRAF5  121:ILGRYQDHLQQCLFQPVQCSNEKCREPVLRKDLKEHLSASCQFRKEKCLYCKKDVVINL  180
mTRAF5  121:----F-----H-S--A-P-P--S---AM----V----Y-R--E-----R-I--T--   180 hTRAF5  181:QNHEENLCPEYPVFCPNNCAKIILKTEVDEHLAVCPEAEQDCPFKHYGCAVTDKRRNLQQ  240
mTRAF5  181:-D----S--A----S---R-VQT-PRAR-N----T---------------T-KG--G--LE  240 hTRAF5  241:HEHSALREHMRLVLEKNVQLEEQISDLHKSLEQKESKIQQLAETIKKLEKEFKQFAQLFG  300
mTRAF5  241:---RA---QD--L------Y---YQ---------------V--F---L---T-M--   300 hTRAF5  301:KNGSFLPNIQVFASHIDKSAWLEAQVHQLLQMVNQQQNKFDLRPLMEAVDTVKQKITLLE  360
mTRAF5  301:R--T--S-V-ALT--T---------RH---I----PSRL---S-VD---S--R--Q--   360 hTRAF5  361:NNDQRLAVLEEETNKHDTHINIHKAQLSKNEERFKLLEGTCYNGKLIWKVTDYKMKKREA  420
mTRAF5  361:AS----VL--G-S--A------N-----Q--A--S------RV----   420 hTRAF5  421:VDGHTVSIFSQSFYTSRCGYRLCARAYLNGDGSGRGSHLSLYFVVMRGEFDSLLQWPFRQ  480
mTRAF5  421:-E-----V----P---------------K-T----------   480 hTRAF5  481:RVTLMLLDQSGKK-NIMETFKPDPNSSSSFKRPDGEMNIASGCPRFVAHSVLENAKNAYIK  539
mTRAF5  481:----------NH-V---A------------S--T---S--T---   540 hTRAF5  540:DDTLFLKVAVDLTDLEDL   557
mTRAF5  541:------------------   558
```

TRAF FAMILY MOLECULES, POLYNUCLEOTIDES ENCODING THEM, AND ANTIBODIES AGAINST THEM

This is a continuation-in-part of: International Application No. PCT/JP97/00512 filed Feb. 24, 1997 which designated the U.S.

TECHNICAL FIELD

This invention relates to a TRAF family molecule, a polynucleotide encoding the molecule, an antibody against the molecule, and an antisense polynucleotide of the polynucleotide encoding the molecule.

BACKGROUND ART

For molecules belonging to the TNF receptor family (hereinafter referred to as "TNF-R"), TNF-R1, TNF-R2, Fas, CD40, CD27, and lymphotoxin-β receptors (hereinafter referred to as "LT-βR" or "TNF-Rrp") are known. These molecules are provided with the function of finally causing the phenomena of the proliferation, cell differentiation, and necrosis of cells by binding to their ligands, or with the function as second signal molecules of other molecules.

Also, TRAF1 and TRAF2 (the abbreviation of TNF-R associated factor), which are molecules capable of associating TNF-R, have been cloned (Goeddel et. al, Cell Vol. 78, No. 4, p. 681–692, 1994) and these are known to associate the domain within the cytoplasm of TNF-R2.

Furthermore, two additional kinds of new TRAF molecules have been identified and the following are noted for these molecules:

(1) TRAF1 associates TNF-R2 and CD40. (J. Biol. Chem. Vol. 269, No. 48, p. 30069–30072.)

(2) TRAF2 plays an important role in activation of the DNA-binding of NF-κB by TNF-R2 or CD40: NF-κB is a nucleoprotein binding to a base sequence comprising 10 base pairs that is within the enhancer region of the Igκ L chain gene and is referred to as "κB motif".

(3) TRAF3 (also referred to as "CRAF1," "CD40bp," or "CAP1") is known to associate TNF-R2, CD40, and LT-βR. (Science Vol. 267, No. 5203, p. 1494–1498; FEBS Lett. Vol. 358, No. 2, p. 113–118; J. Biol. Chem. Vol. 269, p.30069–30072; and Cell Vol. 80, No. 3, P. 389–399.)

(4) As for TRAF4 (also referred to as "CART1"), no molecule has yet been identified to associate it. (J. Biol. Chem. Vol. 270, No. 4, P. 25715–25721, 1995.)

Moreover, it has been reported that neither TRAF1 nor TRAF3 induces activation of the DNA-binding of NF-κB. (Cell Vol. 81, p.495–504; Science Vol. 269, p.1424–1427; and Proc. Natl. Acad. Sci. USA, Vol. 93, p.9699–9703.)

Molecules of the TRAF family are structurally characterized by having TRAF domains, and some members of the family molecules have ring finger motifs, Zn finger motifs or leucine zipper motifs at their N-termini, or coiled coil structures at their centers. Because of these structural features, it is presumed that these TRAF family molecules form complexes in a homo- or hetero-fashion and function as transcription factors.

DISCLOSURE OF THE INVENTION

An object of this invention is to provide a novel TRAF family molecule. Another object of the invention is to provide a substance capable of having an application in the elucidation of functions of the TRAF family molecules, such as an antibody or a polynucleotide probe: namely, the elucidation of interaction between the TRAF family molecules and the elucidation of the signal transduction system of the TNF-R family. A further object of the invention is to provide an antisense polynucleotide applicable to the development of pharmaceuticals.

Specifically, an object of the invention is to provide the screening for the TRAF5 molecule, which is a novel TRAF family molecule according to the invention, isolation and structural determination thereof, as well as to provide a variety of functions that the molecule possesses.

In other words, the object of the invention is as follows: homology with respect to TRAF1 and TRAF2 is analyzed by computer; various oligo-DNA primers capable of amplifying the region that is most highly conserved are synthesized; cDNA is prepared from RNA that is derived from different kinds of cell strains and tissues; PCR is performed using the oligo-DNA primers and the cDNA as a template; and the thus obtained novel gene (TRAF5 gene) exhibiting a high degree of homology to the TRAF1 and TRAF2 genes as well as the amino acid sequence of the TRAF5 molecule encoded by the gene is provided.

In the present specification, the protein will be hereinafter referred to as "TRAF5 molecule" or "TRAF5" and the TRAF5 gene itself referred to as "TRAF5 gene."

It is also an object of the invention to provide information that the TRAF5 molecule tends to associate LT-βR and CD30 and further that it has the ability to induce the DNA-binding activity of NF-κB, which is a DNA-binding protein.

In addition, an object of the invention is to provide means for elucidating the functions of the TRAF5 molecule as well as to provide means for elucidating the signal transduction system of the TNF-R family involving the TRAF family molecules by preparing antibodies against the TRAF5 molecule and using the antibodies.

A still further object of the invention is to provide means for making the TRAF5 gene applicable to experimental probes, probes diagnosing the gene or the antisense genes, and therapeutic agents.

More specifically, this invention provides novel TRAF family molecules as described below, including the TRAF5 molecule.

1. A TRAF family molecule having the properties as noted in (1)–(4) in the following:

(1) Having the ability to associate lymphotoxin-βreceptors (LT-βR) and CD30;

(2) Having the ability to induce the DNA-binding activity of a DNA-binding protein;

(3) Having the inability to associate CD40 or TNF-R2; and (4) Having a leucine zipper motif or coiled coil structure within its molecule.

2. The TRAF family molecule as described above wherein the DNA-binding protein is NF-κB.

3. The TRAF family molecule as described above wherein said molecule is a protein encoded by DNA hybridizing to the base sequence set forth in SEQ ID No. 2 of the Sequence Listing under stringent conditions.

4. The TRAF family molecule as described above wherein said molecule has at least part of the amino acid sequence set forth in SEQ ID No. 1 or SEQ ID No. 3 of the Sequence Listing.

5. A TRAF5 molecule comprising the amino acid sequence set forth in SEQ ID No. 1 of the Sequence Listing.

6. A TRAF5 molecule comprising the amino acid sequence set forth in SEQ ID No. 3 of the Sequence Listing.

7. A TRAF family molecule comprising a modified TRAF5 molecule, said TRAF5 molecule comprising the amino acid sequence which is derived by modifying a part of the amino acid sequence set forth in SEQ ID No. 1 or SEQ ID No. 3 of the Sequence Listing, by substitution, deletion or addition of amino acid(s) without substantially altering the functions of the TRAF family molecule.

8. A TRAF5 molecule comprising an amino acid sequence of from position 233 to position 558 of the amino acid sequence set forth in SEQ ID No. 1 of the Sequence Listing.

9. A TRAF5 molecule comprising an amino acid sequence of from position 342 to position 558 of the amino acid sequence set forth in SEQ ID No. 1 of the Sequence Listing.

10. A TRAF5 molecule comprising an amino acid sequence of from position 233 to position 557 of the amino acid sequence set forth in SEQ ID No. 3 of the Sequence Listing.

11. A TRAF5 molecule comprising an amino acid sequence of from position 342 to position 557 of the amino acid sequence set forth in SEQ ID No. 3 of the Sequence Listing.

12. A polynucleotide encoding the TRAF family molecule as described above.

13. A TRAF5 gene comprising the base sequence set forth in SEQ ID No. 2 of the Sequence Listing.

14. A TRAF5 gene comprising the base sequence set forth in SEQ ID No. 4 of the Sequence Listing.

15. A polynucleotide comprising part of the polynucleotide according to any of Items 12–14 as described above, said part being 12 or more consecutive bases.

16. A polynucleotide comprising part of the polynucleotide according to any of Items 12–14 as described above, said part being 16 or more consecutive bases.

17. An antibody directed against the TRAF family molecule according to any of Items 1–11 as described above.

18. An expression vector comprising a polynucleotide encoding the TRAF family molecule according to Item 12 as described above.

19. A transformant characterized by being transformed with the expression vector as described above.

20. A method of producing a TRAF family molecule, said method comprising using the transformant as described above.

21. An antisense polynucleotide of a polynucleotide encoding the TRAF family molecule according to Item 12 as described above.

22. A polynucleotide comprising part of the antisense polynucleotide as described above, said part being 12 or more consecutive bases.

23. A polynucleotide comprising part of the antisense polynucleotide as described above, said part being from 16 or more to 30 or less consecutive bases.

24. A derivative of the polynucleotide according to any of Items 12–16 or Items 21–23 as described above.

BRIEF DESCRIPTION OF THE DRAWINGS

FIG. 6A is a graph showing a primer used to identify the murine TRAF5 gene.

FIG. 6B is a graph showing a primer used to identify the murine TRAF5 gene.

FIG. 11 is a graph showing a comparison between the amino acid sequence of the human TRAF5 molecule (SEQ ID NO:3) and the amino acid sequence of the murine TRAF5 molecule (SEQ ID NO:1), where the upper row represents the amino acid of the human TRAF5 molecule and the lower row represents the amino acid of the murine TRAF5 molecule; "–" in the murine TRAF sequence indicates the amino acid at an indicated position being identical with its corresponding amino acid of human TRAF5 (i.e., the amino acid depicted in the upper row); and "–" at number 494 of the human TRAF5 sequence indicates deletion of an amino acid at the position in question.

BEST MODE FOR CARRYING OUT THE INVENTION

Figure 1:
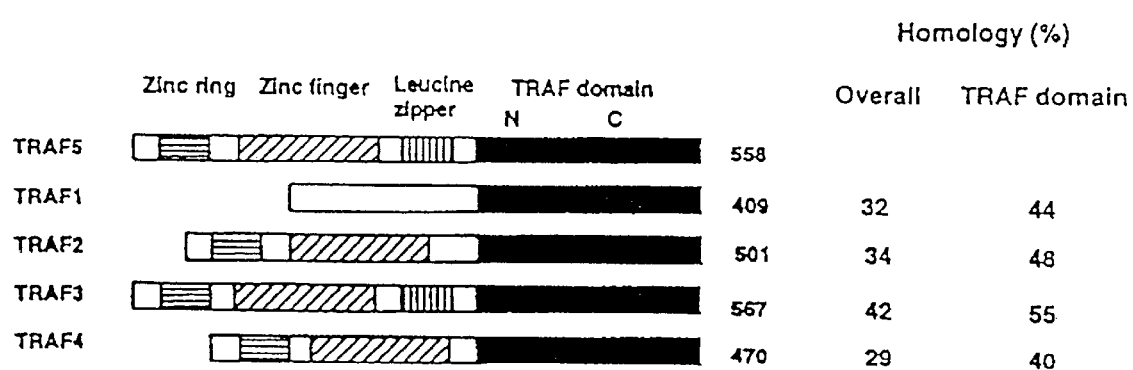
FIG. 1 is a graph showing the results of a homology analysis of the amino acid sequences for the TRAF5 molecule and other TRAF family molecules, where the blacked part represents a TRAF domain, the vertically lined part represents a leucine zipper motif, the obliquely lined part represents a Zn finger motif, and the horizontally lined part represents a Zn ring finger motif; with respect to TRAF1–TRAF4, amino acid homology in their overall sequences and their TRAF domains against TRAF5 is indicated on the right-hand side.

This invention will be explained in detail hereinbelow.
(Identification of Novel TRAF Family Molecules)
The novel TRAF family molecules according to this invention and methods for identifying polynucleotides encoding the TRAF family molecules according to the invention will concretely be illustrated below.

First, in order to find a high homology region in TRAF family molecules, the known base sequences of TRAF1 and TRAF2 are screened for homology and the high homology region between the two is specified for selection.

Secondly, primers are designed to perform the PCR amplification (polymerase chain reaction) of the specified region. The base sequences of the primers for such a purpose are not particularly limited, but for example, preferably usable is a mixture of primers of 17 mer bases to which EcoRI sites are appended, as shown in FIGS. 6A and 6B. In addition, such primers can be synthesized using a standard DNA synthesizer.

In FIG. 6A "A" represents adenine, "T" thymine, "G" guanine, "C" cytosine, "Y" cytosine or thymine, "N" adenine or thymine or guanine or cytosine, "R" adenine or guanine, and "D" any base of adenine, thymine and guanine. Thus, (1) in FIG. 6A (SEQ ID NO:14) represents 256 kinds of primers and (2) in FIG. 6B (SEQ ID NO:15) represents 768 kinds of primers.

Furthermore, the selection of DNA that serves as a template is not particularly limited in this invention, but in practice mRNA may preferably be prepared from murine B cell lymphoma, murine monocyte cell strains, and murine liver, and then cDNA may preferably be prepared using oligo-dT or a random hexamer as a primer.

In addition, the cells for the purpose of preparation of the mRNA are not limited to the above-mentioned cells in the invention.

Preparation of the mRNA, for example, can preferably be carried out with ease using an Oligo-dT cellulose column after total RNA fractions have been obtained by the thiocyanic acid guanidine method or the like (Biochemistry Vol. 13, p. 2633, 1974).

The PCR is performed using the above-mentioned primers and the cDNA pool obtained as described above as a template. The amplified fragment is then recovered and is subcloned into a cloning vector having a muticloning site: pBluescript SK(+) is preferably usable, for example. DNA sequencing is conducted on this subcloned product with a DNA sequencer according to the dideoxy method, revealing it to be a novel gene. Such method will provide novel TRAF family gene fragments. This novel TRAF family gene is labeled with $^{32}P$ to give one that serves as $^{32}P$-TRAF fragment. In carrying out the dideoxy method, either a primer method relying on primers labeled with fluorescent dyes or a dye terminator method relying on ddNTP labeled with fluorescent dyes can preferably be used.

On the other hand, Poly(A)RNA is newly prepared from a monocyte cell strain or a tissue such as liver tissue and then, a cDNA library is constructed from this. Any of phage vectors such as λgt10, λgt11, and λZAP11 and plasmid vectors such as pBR and pUC is usable for this cDNA library.

The cDNA library thus prepared is screened using the aforementioned $^{32}P$-TRAF fragment as a probe, and a clone containing cDNA that covers the whole translational region of TRAF5 can be obtained. Next, its base sequence is determined using a DNA sequencer.

Further, specific examples for the method to obtain a murine TRAF5 gene are shown in the Examples of the present specification as will be illustrated below. It is possible to screen for and obtain TRAF5 genes from other animals, including human, by employing cDNA libraries that are prepared from the cells of desired animal species in a similar manner to the method as described above.

The structure of a TRAF5 gene, for example in the murine case, is shown as SEQ ID No. 2 of the Sequence Listing. The murine TRAF5 comprises an open reading frame of the 1674 residue nucleotide (a portion from position 323 to position 1999 of the SEQ ID of the Sequence Listing), namely 558 amino acid residues. The size of its mRNA is assumed to be 2.2 kb.

The amino acid sequence of the murine TRAF5 molecule encoded by the above-mentioned base sequence is shown in SEQ ID No. 1 of the Sequence Listing. Referring to FIG. 1, the amino acid sequence is compared to the known TRAF family molecules. Structurally, the TRAF5 molecule resembles the TRAF3 molecule. The TRAF5 molecule differs from the TRAF1, TRAF2, or TRAF4 molecule in that it has a leucine zipper motif or a coiled coil structure.

Also, as FIG. 11 shows, very high homology exists between the amino acid sequence of the murine TRAF5 molecule and the amino acid sequence of the human TRAF5 molecule and its functions are well preserved between the different species.

The TRAF5 genes show high homology between a mouse and human. Therefore, a TRAF5 gene can also be obtained from the desired animal species, according to the method of Example 7 as will be described later: namely, the method in which part or the whole of the TRAF5 gene already in possession is used as a probe to isolate the TRAF5 gene of the desired animal from a cDNA library that originates in the animal by following a cDNA cloning method such as the plaque hybridization method, which is conventionally employed.

(Analysis of the Functions of TRAF Family Molecules of This Invention)

Screening is possible for TNF-R family molecules that the TRAF5 molecules of the invention tend to associate, according to the method as described below, for example.

First, a fusion protein is prepared using an expression vector system for the fusion protein. Specifically, preferably usable is a method in which the domain part within the cytoplasm of a TNF-R family molecule is inserted into the downstream region of glutathione-S-transferase (GST) to prepare the fusion protein. In this invention, those other than GST which can synthesize fusion proteins with TNF-R family molecules are usable. Concretely, expression systems for thioredoxin fusion proteins, e.g., Thio Fusion (Registered Trademark, available from Invitrogen Inc.) and for fusion proteins with leader peptides derivable from gene 10 of T7 can also be used.

Moreover, to easily detect the TRAF5 molecule, the TRAF5 gene is translated in vitro to prepare a TRAF5 molecule labeled with $^{35}S$-methionine or the like, which enables detection of the TRAF5 molecule.

Next, fusion proteins and the TRAF5 molecule are mixed and a fusion protein having associated the TRAF5 molecule is selected. For the method of selection, a method to have any associated substance adsorbed onto a GSH-agarose column can be used, for example, and in addition, chromatographic operations such as affinity chromatography can also preferably be used.

To ascertain the ability to associate, after the associated substance has been separated and heated to dissociate the TRAF5 molecule, SDS-PAGE is conducted and the gel is autoradiographed, thus detecting the presence of the band of the TRAF5 molecule. Thereby, it becomes possible to ascertain that the TRAF5 molecule has the ability to associate LT-βR and CD30.

Also, after both the TRAF5 molecule and LT-βR have been forced to express in the same animal cells, any associated substance in the cells is subjected to the immunoprecipitation blotting: this method also enables confirmation of the association between the TRAF5 molecule and LT-βR. Specifically for this purpose, the TRAF5 molecule to be used should preferably be bound to the hemagglutinin epitope (HA epitope) of influenza virus which serves as a tag. Alternatively, preferably usable is a method in which the leader peptide derivable from gene 10 of T7 as described previously has been bound to the molecule. Further, although a variety of methods known in the art can be used for the method of binding a tag as described previously, genetic engineering methods are preferable in this invention. Especially, after treatment with restriction enzymes such as EcoRI, DNA encoding the HA epitope and the TRAF5 molecule that has been amplified by PCR are preferably incorporated into an expression vector.

Where the TRAF5 molecule is to be prepared by a genetic engineering method, it is also preferable that an expression vector for the TRAF5 molecule and a vector into which LT-βR has been incorporated be introduced into cells. As to the method for introducing vectors into cells, a liposome method, an electroporation method, and others can be used, but particularly, it is preferable to use a DEAE-dextran method (available from Pharmacia Inc.).

Furthermore, if an antibody against the epitope bound as a tag (anti-HA antibody in the case where the HA epitope is bound) is added to the cell product and is allowed to react thereto, it is possible to separately and precisely collect the TRAF5 molecule from any substances associating the TRAF5 molecule.

As previously noted, the TRAF5 molecules of this invention have the ability to associate LT-βR and CD30, which are TNF-R family molecules. Such a property can be used to elucidate the functions of TNF-R family molecules. The TNF-R and TNF family molecules are a group of important molecules that are the trigger for causing the differentiation, proliferation, and death of cells; therefore, use of the TRAF5 molecules, genes thereof, and antibodies against them makes it possible to elucidate such functions and then to elucidate the mechanisms of cancer and apoptosis.

Similar to LT-α, LT-βR is also presumed to have an important role in differentiation of the immune system. Hitherto, it has been known that the differentiation of peripheral lymphonodi is immature in mice deficient in the LT-α gene, and it is believed that so is the case with LT-βR. As for the functions of CD30, it is known that in the deficient mice, the T cells can not normally differentiate within their thymi and the signals often do not transmit well through T cell receptors. Thus, that the TRAF molecule is a substance to be the key factor in the signal transduction of LT-βR suggests association between the TRAF5 molecule and LT-βR, or CD30. It is then presumed that the mice deficient in the TRAF5 molecule cause immatureness of their immune systems, e.g., immatureness in the differentiation of their peripheral lymphonodi.

Next, the TRAF5 molecules of this invention are used to examine cells' action of signal transduction. This makes it possible to ascertain that the expression of the TRAF5 molecule induces activation of the DNA-binding of NF-κB which is a DNA-binding protein. In other words, it is ascertained that the TRAF5 molecules can be used to induce activation of the DNA-binding of a DNA-binding protein.

In this invention, it can be also ascertained 5 that with the use of the TRAF5 molecule according to the invention, the expression of LT-βR alone causes the expression of NF-κB, but that this activation is inhibited by adding an excess of only a portion of from position 233 to position 558 of the murine TRAF5 molecule which is a deleted protein. Namely, by utilizing the portion of positions 233–558 of the TRAF5 molecule, it becomes possible to study its action to antagonize LT-βR. The preparation of the TRAF5 molecules or TRAF5 genes according to this invention also enables the study on a system controlling the signal transduction involving NF-κB, as well as the development of drugs.

Employing a polynucleotide probe containing the binding site of NF-κB, the NF-κB bound to the probe is to be detected in the cells where the TRAF molecule has been expressed: for example, this method can be used to ascertain this. The TRAF5 molecule to be used may be part thereof or the whole molecule. The polynucleotide probe containing the binding site of NF-κB may be the gene of NF-κB itself or part thereof, and may be of natural or synthetic origin. For the method of detection, Electrophoretic Mobility Shift Assay (EMSA) may be employed, for example. Other than this, the gel shift method may be usable.

As noted above, the TRAF family molecules of this invention are provided with the property of associating LT-βR and CD30, and capable of inducing the DNA-binding activity of a DNA-binding protein. For the DNA-binding protein to ascertain its DNA-binding activity, NF-κB is preferable.

Further, among the known TRAF family molecules, the TRAF3 molecule is structurally similar to the TRAF5 molecule. Based on the information obtained in this invention concerning the association with LT-βR and CD30 in addition to the activation of NF-κB, it has been verified that the TRAF3 molecule neither associate TNF-R2 nor CD40 and is not able to activate NF-κB. Thus, it is different from the TRAF5 molecules according to this invention.

(TRAF Family Molecules of This Invention)

The properties that characterize the TRAF family molecules of this invention are summarized in the following four points:

(1) They have the ability to associate lymphotoxin-β receptors (LT-βR) and CD30.
(2) They have the ability to induce the DNA-binding activity of DNA-binding proteins.
(3) They have the inability to associate CD40 or TNF-R2.
(4) They have a leucine zipper motif or a coiled coil structure within their molecules.

Insofar as the TRAF family molecules of the invention have the above-mentioned properties, they embrace ones that contain at least parts of the amino acid sequence set forth in SEQ ID No. 1 or SEQ ID No. 3 of the Sequence Listing. Although the part of the amino acid sequence as described above is not particularly limited, the one of from position 233 to position 558 of the amino acid sequence set forth in SEQ ID No. 1 of the Sequence Listing is preferable. Especially, it may preferably have the TRAF domain (positions 342–558 of the amino acid sequence set forth in SEQ ID No. 1 of the Sequence Listing).

Insofar as the TRAF family molecules of the invention have the above-mentioned properties, they also embrace proteins encoded by DNAs hybridizing to part of the amino acid sequence set forth in SEQ ID No. 2 of the Sequence Listing, as will be illustrated in Example 7.

Insofar as the TRAF family molecules of the invention have the above-mentioned properties, they also embrace the TRAF family molecule part of which has been structurally modified by substitution, deletion or addition of amino acid(s). For the method of substitution, deletion or addition of amino acid(s), techniques known in the art are usable, for example, as described in "Molecular Cloning 2nd edition," p. 15.1–15.113.

(The Polynucleotides of This Invention Encoding TRAF Family Molecules)

The polynucleotides of the invention encoding TRAF family molecule are, for example, a DNA and a RNA corresponding to the DNA, which DNA comprises the base sequence of from position 323 to position 1999 of the base sequence of SEQ ID No. 2 of the Sequence Listing. These are polynucleotides encoding the murine TRAF5 molecule comprising the amino acid sequence of SEQ ID No. 1 of the Sequence Listing. The whole or part of the coding region of the protein can be expressed in suitable transformants, which can be used to produce recombinant TRAF family molecules.

In addition, part of the polynucleotide can immediately be used as polynucleotide probes for research purposes that aim at investigating the presence of genes encoding the TRAF family molecules in tissues or cells, as well as their expression state. Preferably, the part to be used as the probe is 12 bases or more and has a GC content of from 30 to 70%. Most preferably, it is 16 bases or more. The polynucleotide to be used as the probe may be a derivative. The polynucleotide may be a base sequence of the noncoding region of the gene coding the TRAF family molecule or its complementary base sequence when it is to be used as the probe.

(The Antibodies of This Invention Against TRAF Family Molecules)

The antibodies of the invention against TRAF family molecules embrace either of polyclonal antibodies and monoclonal antibodies insofar as they recognize the TRAF family molecules. They also embrace active fragments thereof and chimera antibodies containing the active fragments.

The antibody, i.e., immunoglobulin, has H and L chains, and is classified into five classes (IgA, IgD, IgE, IgG, and IgM) based on its physicochemical immunological properties. Among these, IgA and IgG are further classified into subclasses with respect to the types of their H chains. The novel antibodies of this invention embrace ones belonging to all these classes and subclasses.

Moreover, the antibody of the invention does not necessarily need to use the whole antibody molecule and can use a portion of the molecule (active fragment) insofar as it is active. As the active fragment, concretely named are $F(ab')_2$, Fab, Fv and recombinant Fv. For example, $F(ab')_2$ results if the antibody is digested with pepsin, and Fab results if digested with papain.

Although these fragments can be used alone, they can be conjugated to substances such as albumin and polyethylene glycol and can be used as new conjugates. In many cases, such conjugates generally exhibit their effectiveness to the maximum degree in vivo without being decomposed for a long period of time. The method for attaching a substance such as albumin or polyethylene glycol to the active fragment is, for example, described in "Antibodies A Laboratory Manual," Cold Spring Harbor Laboratory, 1988, p. 77–81 and p. 129–137. In general, employing divalent-reactive reagents such as SPDP (available from Pharmacia Inc.), SMPB (available from Pierce Inc.), and EMCS (Dotite Inc.), the active fragments can be easily conjugated to albumin or the like.

Also, employing an active fragment, the primary structure (e.g., Fc) other than the region (e.g., hypervariable region) necessary for reaction with the TRAF family molecule in the H and L chains is substituted by the corresponding primary structure of an antibody derived from other animal species: this or a similar method can yield chimera antibodies.

The novel antibodies of this invention can be obtained according to methods known in the art, regardless whether they may be polyclonal antibodies or monoclonal antibodies. For example, they can be obtained by referring to "Immunological Experimental Procedures," edited and published by The Immunological Society of Japan. With respect to the TRAF family molecules of this invention to be used as immunogens, the method of obtaining the TRAF family molecules should not be questioned insofar as they have such purity as will allow their use for preparation of the antibodies.

Where the TRAF family molecule to be used as the immunogen is a TRAF family molecule with a low molecular weight or part thereof (namely a TRAF family molecule comprising about 10 to about 20 amino acid residues or a portion thereof), it may be conjugated to a carrier such as keyholelymphethemocyanine (KLH) and used as an antigen.

Animals to be immunized with the TRAF family molecules or parts thereof may be any animal other than human. Among animals that are used by those skilled in the art, animal species capable of producing the desired antibodies may preferably be selected for use.

The polyclonal antibodies may be obtained by purifying the resulting antisera. The purification can be a combination of the methods such as salting out, ion-exchange chromatography, and affinity chromatography.

The monoclonal antibodies may be obtained by the method for preparing hybridomas. For the cell fusion, techniques using polyethylene glycol, Sendai virus, electric pulse, etc. are available.

Other than the above, genetic engineering methods can also be used to obtain the antibodies. For example, mRNA is extracted from the spleen cells or lymphocytes of an animal immunized with the TRAF family molecule or part thereof, or from the hybridoma producing a monoclonal antibody against the TRAF family molecule or part thereof, from which a cDNA library is prepared. The antibodies are expressed using the cDNA library. The clones producing the antibodies reactive to the antigens are obtained by screening the cDNA library, the obtained clones are cultured, and the desired antibodies can be purified from the cultured mixture by the combination of methods such as salting out, ion-exchange chromatography, and affinity chromatography.

The antibodies of this invention can be used to detect the TRAF family molecule or part thereof existing in body fluids or tissues. The antibodies can also be used to prepare antibody columns for use in purification of the TRAF family molecule or part thereof, as well as to detect the TRAF family molecule or part thereof in their fractions.

(Recombinant Vectors and Transformants)

The recombinant vectors and transformants of this invention are characterized by containing the whole or parts of the genes encoding the TRAF family molecules. These can be prepared according to a variety of methods as shown in Examples 1, 4, 5, and 7. Any of bacteria such as *E. coli,* yeast, animal cells can be used as a host for the transformants.

Further, these may find their utility, for example, in the production of the whole or part of the TRAF5 molecule as shown in Examples 4 and 5, i.e., in the method for production of a TRAF family molecule according to this invention, or may be intended for use in obtaining the whole or part of the TRAF5 gene in a large quantity as shown in Examples 1 and 7.

(Method for Production of TRAF Family Molecule According to This Invention)

According to the method of this invention for production of a TRAF family molecule, the transformant of the invention is first grown and the gene is amplified and expressed. Next, the culture is recovered and, if necessary, manipulations such as concentration, solubilization, dialysis, and various kinds of chromatography are conducted to purify the TRAF family molecule of the invention.

A variety of references are available for the cultivation of the transformants, and for example, it can be carried out according to the method as described in "Microorganism Experimental Methods," The Japanese Society of Biochemistry, Incorporated Foundation, ed. Tokyo Kagaku Dojin, 1992.

The purification methods involve salting out, ultrafiltration, isoelectric precipitation, gel filtration, electrophoresis, ion-exchange chromatography, hydrophobic chromatography, a variety of affinity chromatography such as antibody chromatography, chromatofocusing, adsorption chromatography, and reverse phase chromatography, and may be carried out by selecting them as appropriate. As the Examples illustrate in detail, the purification is preferably done by means of affinity chromatography using LT-βR and CD30 or that using the antibodies of this invention.

Also, in the method for production, the TRAF family molecule to be prepared may be produced by the transformant as a fusion peptide with other polypeptides. In this case, if necessary, the manipulations of treatment with a chemical substance such as bromocyanogen or an enzyme such as protease and slicing out the TRAF family molecule are added to the purification step.

(The Antisense Polynucleotides of This Invention)

The antisense polynucleotides of this invention embrace all of those in which a plurality of nucleotides comprising bases, phosphoric acid, and sugars are bonded, including those not present in nature; their representatives are DNA and mRNA.

The antisense polynucleotides of the invention find a use for the polynucleotide probes for research purposes that aim at investigating the presence of genes encoding the TRAF family molecules, as well as the state of their expression.

Also, another use of the antisense polynucleotides of the invention is to regulate the expression of TRAF family molecules. It is expected that the antisense polynucleotide hybridizes to DNA encoding the TRAF family molecule or to MRNA encoding the TRAF family molecule and promotes or suppresses the expression of the TRAF family molecule. Therefore, the antisense polynucleotides can be used as therapeutic agents for disorders in the signal transduction system involving the TRAF family molecules or for disorders involving the LT-βR-mediated signals. In other words, antisense drugs can be developed based on the polynucleotides and derivatives thereof.

Employing a polynucleotide containing the base sequence complementary to DNA or mRNA that encodes a protein, expression of the protein is to be regulated: this method is referred to as "antisense method" and is the technology currently being pursued by many researchers. The polynucleotide having the complementary sequence is believed to regulate expression of the protein by binding to DNA or mRNA that carries genetic information at any of the following stages and influencing the normal flow of transmission of genetic information: (1) transcription stage from the gene to pre-mRNA; (2) processing stage from the pre-mRNA to mature mRNA; (3) passing stage through nuclear membranes; and (4) translation stage to the protein.

In view of the ease of hybridization, it is thought to be advantageous that polynucleotides or polynucleotide derivatives having the base sequences complementary to the base sequences of regions that form stem loops be designed. (Clinical Immunology, vol. 25, p. 1200–1206, 1993.)

It is also expected that the polynucleotides having the base sequences complementary to the base sequences in the vicinity of translation start codons, or at the sites of ribosomal binding, capping and splicing have, in general, a great inhibitory effect on expression. (Cancer and Chemotherapy, Vol. 20, No. 13, p. 1899–1907.) Thus, a great expression regulatory effect is expected for the antisense polynucleotides of this invention that contain the genes encoding the TRAF family molecules or the base sequences complementary to the base sequences of mRNA against the genes in their vicinity of translation start codons, or at their sites of ribosomal binding, capping and splicing.

Also, for the antisense polynucleotide, the length on the order of from 16 to 30 bases is preferable for use in the regulation of expression.

(The Polynucleotide Derivatives of This Invention)

The polynucleotides and antisense polynucleotides of the invention embrace all those analogous to the polynucleotides existing in nature with respect to their stereochemical structures or functions, insofar as the sense polynucleotides can express the TRAF family molecules of the invention and the antisense polynucleotides can hybridize to their complementary polynucleotides (sense polynucleotides). For example, they may be polynucleotides 3'- or 5'-termini of which are bound to other substances, or may be substances having undergone modifications such as substitution, deletion, and addition in at least part of any of base, sugar, and phosphoric acid of the polynucleotide, or those having bases, sugars or phosphoric acid not present in nature, or those having skeletons other than sugar-phosphoric acid skeletons.

Also, the derivatives should preferably be ones that have enhanced activity in at least one of nuclease resistance, tissue selectivity, cell permeability, and binding strength. It is known that especially preferred polynucleotide derivatives have phosphorothioate bonds as their skeleton structures. The polynucleotides and derivatives thereof according to this invention also embrace derivatives having these functions or structures.

For example, among the derivatives, there are ones which can be synthesized using a chemical synthesizer (e.g., Type 394 available from Perkin Elmer Inc.), such as the methylphosphonate type and the phosphorothioate type. In this case, manipulations are conducted following the manual as attached to a chemical synthesizer and the synthesized products as obtained are purified by HPLC methods such as reverse phase chromatography; thus, the desired polynucleotide derivatives can be obtained.

The contents of Application No. 034674/1996, filed Feb. 22, 1996, in Japan is hereby incorporated by reference.

EXAMPLES

This invention will be further detailed by illustrating examples below; however, the invention is not to be limited to these examples.

Example 1

Identification of the TRAF5 Molecule

1. The Design of Primers

The base sequences for TRAF1 and TRAF2 were screened for a high homology region. The portion from Tyr to Gly of the amino acid sequence of TRAF1, namely Tyr Leu Asn Gly Asp Gly (YLNGDG) (SEQ ID NO:9), was designated a sense side and the amino acid sequence, Asp Asp (Thr/Ala) (Ile/Met) Phe (Ile/Leu) (DD(T/A) (I/M) F (I/L)(SEQ ID NO: 10 and for alternative amino acids, (SEQ ID NO: 11), was designated an antisense side. With respect to the sense side, a sense chain of the gene encoding its amino acid sequence was synthesized as a primer; with respect to the antisense side, an antisense chain of the gene encoding its amino acid sequence was synthesized as a primer. Here, "(I/M)" as described in the above-mentioned amino acid sequence means either of "I" and "M." The base sequence encoding an amino acid sequence can not be singularly determined because of degeneration: for example, if the amino acid is Ala, there are four conceivable cases-GCA, GCG, GCC, and GCT. In such a case, the synthetic mode during the automated DNA syntheses is selected to be GCX ("x" contains all of A, G, C, and T) and a mixture of oligo-DNA primers that correspond to the selected amino acid sequences was prepared. These primers are shown in FIGS. 6A and 6B. Here, FIG. 6A represents 256 kinds of the sense side primer, whereas FIG. 6B represents 768 kinds of the antisense side primer. The mixture of oligo-DNA primers as described above contains all these. Furthermore, each primer was designed to contain an EcoRI site, as is shown in FIGS. 6A and 6B.

2. Preparation of cDNA Mixture (1) Murine B cell lymphoma A20.25 (ATCC TIB208) was grown in a 25-cm² flask.

(2) After recovery and washing with PBS, the cultured cells were suspended in 1 ml of PBS and the cell number was counted.

(3) The cells ($1 \times 10^6$) were taken into an aseptic Eppendorf tube and centrifuged at 5,000 rpm for 3 min to remove the supernatant. The pellet was subjected to tapping.

(4) RNAZ01B (Registered Trademark, available from CosmoBio Co. Ltd.) 200 μl was added and thoroughly stirred with the tip of a pipetteman to dissolve the cells.

(5) After 20 μl of chloroform was added and shaken, the cells were allowed to stand in ice for 5 min. Subsequently, they were centrifuged at 15,000 rpm for 15 min at 4° C. to recover the colorless, transparent portion of the upper layer, which was then transferred to a new tube.

(6) Next, after centrifugation at 15,000 rpm for 15 min at 4° C., the supernatant was discarded, 800 μl of 75% ethanol was added to the pellet, and it was allowed to stand at −20° C. for 30 min.

(7) Next, after centrifugation at 15,000 rpm for 15 min at 4° C., 11.5 μl of distilled water was added to the pellet.

(8) Next, oligo-dT (0.5 mg/ml) 0.5 μl was added and it was allowed to stand at 70° C. for 10 min and on ice for 5 min.

(9) Next, a solution having the composition as described below was added and it was allowed to stand at 42° C. for 50 min, at 90° C. for 5 min, and on ice for 5 min.

| | |
|---|---|
| 5 × RT Buffer | 4 μl |
| 10 mM dNTPmix | 1 μl |
| Superscript RTase | 1 μl |

(Registered Trademark, Available from GibcoBRL Inc.)

(10) RNaseH (Registered Trademark, available from GibcoBRL Inc.) 1 μl was added and it was allowed to stand at 37° C. for 20 min, affording the cDNA mixture.

3. PCR (1) Employing the cDNA mixture obtained in 2 and the oligo-DNA primers obtained in 1, PCR was performed under the following conditions:

| | |
|---|---|
| CDNA | 2 μl |
| dNTPmix | 1 μl |
| Primer (sense side) (100 pmol/l μl) | 1 μl |
| Primer (antisense side) (100 pmol/l μl) | 1 μl |
| 10 × PCR Buffer | 4 μl |
| DDW | 30.5 μl |
| Ampli-Taq | 0.5 μl |
| Total | 40 μl |

Mineral oil (40 μl) was overlaid on the above composition and it was allowed to stand at 94° C. for 5 min. Thereafter, the following cycle was repeated 40 times for reaction: at 45° C. for 2 min, followed by at 72° C. for 1 min, and-followed by at 94° C. for 1 min. Of note in this reaction was that the temperature of annealing had been set at as low as 45° C. to design such that low homology ones could be picked up as many as possible.

(2) After reaction, the PCR product was electrophoresed on a mini gel (1.5% agarose gel).

(3) A band was sliced out from the gel: the band was believed to be the gene encoding the about 0.5 kb TRAF domain (the portion of from position 342 to position 558 of the amino acid sequence of SEQ ID No. 1 of the Sequence Listing). PCR product was recovered from this by means of Gene CleanII (Registered Trademark, available form BIO 101 Inc.).

(4) Further, part of the recovered product was again subjected to the mini gel electrophoresis as described above, thus ascertaining that a band appeared at about 0.65 kb.

4. DNA Ligation

Employing a Bluescript vector (available from Stratagene Inc.), DNA ligation was carried out in a reaction medium having the following composition:

| | |
|---|---|
| ADDW | 5 μl |
| 10 × Ligation buffer | 1 μl |
| PCR Vector | 2 μl |
| PCR Product | 1 μl |
| T4DNA Ligase | 1 μl |
| Total | 10 μl |

Reaction was carried out at 14° C. overnight to give a ligation mixture.

5. Transformation

Transformation was performed using a Bluescript cloning kit.

(1) To a cell suspension (5 μl) on ice were added 2 μl of 0.5 M β-mercaptoethanol and the ligation mixture prepared in (4), and allowed to stand for 30 min. Subsequently, it was allowed to stand in a hot water bath at 42° C. for 30 sec and then, on ice for 20 min. A SOC medium (450 μl) was added, and it was incubated at 225 rpm for 1 h at 37° C.

(2) Next, the incubated medium was spread onto LB agar plates (+ampicilline, X-Gal, and IPTG) at 50 μl, 100 μl, and 200 μl, respectively.

(3) After incubation at 37° C. for 18 h, the incubated products were allowed to stand at 4° C. for 2 h and colonies in white and in blue appeared.

6. Culturing on Miniscale (1) Ninety-six white colonies were picked up from the respective plates prepared in 5.

(2) One of the aforementioned colonies was added to a 3-ml LB medium (+Amp) and shaken at 37° C. overnight.

7. Preparation on Miniscale

According to the method as described in "Molecular Cloning 2nd Edition," Cold Spring Harbor Laboratory, 1989, p. 1.25–1.28, the following manipulations were conducted.

(1) The cultured preparation (1.5 ml) was taken into an Eppendorf tube: the remaining preparation was spread, and cultured at 37° C. and preserved. It was centrifuged at 6,000 rpm for 2 min at 4° C.

(2) Solution 1, 100 μl (lysozyme 5 mg/ml) was added to the pellet and it was allowed to stand at room temperature for 5 min. Subsequently, Solution 2 (200 μl) that had been gently mixed on ice for 5 min was added, Solution 3 (150 μl) that had been mixed on ice for 15 min was added and next, centrifugation was carried out at 12,000 rpm for 5 min at 4° C. For the composition of each solution, the above-mentioned "Molecular Cloning 2nd Edition" was followed.

(3) The supernatant was taken into a new Eppendorf tube. To this was added an equal volume of phenol, and then, centrifugation was carried out at 12,000 rpm for 1 min at room temperature.

(4) The supernatant was taken into a new Eppendorf tube. To this was added an equal volume of a mixture of $CHCl_3$: iAA (99:1) and then, centrifugation was carried out at 12,000 rpm for 1 min at room temperature.

(5) The supernatant was taken into a new Eppendorf tube. To this was added 1 μl of Mussel glycogen and 900 μl of ethanol and after allowing it to stand at −80° C. for 30 min, centrifugation was carried out at 15,000 rpm for 5 min at 4° C.

(6) The precipitates were dried. To this were added 20 μl of TE and 1 μl of RNase A (5 mg/ml) and it was allowed to stand at 65° C. for 20 min, affording a plasmid DNA.

(7) Electrophoresis on a mini gel was conducted under the conditions as described below to examine the bands.

| | |
|---|---|
| H Buffer | 1 μl |
| EcoRI | 1 μl |
| DNA | 1 μl |
| ADDW | 7 μl |
| Total | 10 μl |

After the plasmid DNA was incubated in the above-mentioned solution at 37° C. for 1 h, it was added onto a 0.75% agarose gel and electrophoresed.

8. DNA Sequencing (1) Plasmid DNA (1 μl) was taken up and diluted with 99 μl of TE.

(2) The absorbance (A260) was measured with an spectrophotometer at 260 nm and DNA values were determined: the DNA concentration (DNA value) of a diluted solution when A260 is 1.0 is 50 μg/ml.

(3) Based on the A260 values, the DNA was diluted with TE so that it reached 1 μg/gl.

(4) DNA sequencing was conducted using a DNA Sequencer Model 373A (available from ABI) according to the dye terminator method.

(5) Following the above-mentioned method, homology was investigated with respect to the 96 clones screened in 6, and as a result, 10 clones (all having the same sequence) of a novel gene belonging to the TRAF family were obtained.

As noted above, part of the novel gene belonging to the TRAF family was provided by lowering the annealing temperature during PCR to 45° C.

9. Construction of cDNA Library

Employing a Uni-ZAP (Registered Trademark, Stratagene Inc.) a cDNA Library kit (available from Stratagene Inc.) and a Poly(A) quick mRNA isolation kit (available from Stratagene Inc.), a cDNA library was constructed according to their respective manuals.

(1) Murine monocyte cell strain J774A.1 (ATCC TIB-67) $1 \times 10^8$ cells were made into total RNA by means of the Uni-ZAP kit.

(2) Using this RNA and the Poly(A) quick mRNA isolation kit (available from Strategene Inc.), 10 μg of Poly(A) RNA was finally obtained.

(3) From this Poly(A)RNA, the cDNA library was constructed using the Uni-Zap kit as previously described.

Other than the present examples, preparation of the Poly (A)RNA and cDNA libraries was also feasible by consulting the protocols as described in references listed in the following: "Molecular Cloning 2nd Edition," Chapter 8; and "Preparation of Gene Libraries; Biomanual Series 2, p. 33–40, and 95–106, Yodo Co. Ltd.

10. Screening for cDNA

In order to obtain cDNA corresponding to the PCR product (clones) that was obtained through Steps 1–8 and that was considered belonging to the TRAF family, hybridization between the PCR product and the cDNA library constructed in 9 was carried out, and a novel cDNA of the novel TRAF family was screened for in the manner described below. The hybridization conditions adopted those as described in "Cell Engineering Experimental Protocols," p. 57–65, Shujun Co. Ltd., 1991.

(1) Employing a random primer labeling kit (available from Takara Shuzo Co. Ltd.) and a $[\gamma\text{-}^{32}P]ATP$ (available from Amasham Inc.), the PCR product obtained in 7 was labeled with $^{32}P$, which served as a DNA probe.

(2) Next, the cDNA obtained in 9 was screened according to the plaque hybridization method (see, "Cell Engineering Experimental Protocols," p. 57–65, Shujun Co. Ltd., 1991.), affording 16 kinds of cDNA clones.

(3) DNA sequencing was conducted. on these 16 kinds of clones, and finally, one clone was selected by excluding clones with partial lengths and those with overlapping sequences. The base sequence of this clone is set forth in SEQ ID No. 2 of the Sequence Listing. Transformed E. coli into which this cDNA was introduced was deposited on Feb. 9, 1996 in the National Institute of Bioscience and Human-Technology, Agency of Industrial Science and Technology, Ministry of International Trade and Industry locating at 1-1-3 Higashi, Tsukuba, Ibaragi, 305 Japan (Accession No: FERM BP-5384).

(4) A computer analysis was performed on the basis of the base sequence of this clone with the full 2224 bp length. As a result, the cDNA was found to contain an open reading frame with 1674 bp. In other words, it was found that the protein encoded by the cDNA comprised a sequence of 558 amino acids. The amino acid sequence is set forth in SEQ ID No. 1 of the Sequence Listing.

(5) Also, as a result of homology comparison between the protein and other TRAF family molecules, it was determined that the protein had homology of 29–42% in its overall length, as is shown in FIG. 1. Particularly, the TRAF domain (the portion of from position 342 to position 558 of the amino acid sequence set forth in SEQ ID No. 1 of the Sequence Listing) had homology of 40–55%. From these results and the protein structure shown in FIG. 1, it was ascertained that the protein is evidently a novel molecule belonging to the TRAF family molecule. Thus, the protein was identified as a novel TRAF family molecule and designated TRAF5 molecule. In FIG. 1, the blacked part represents a TRAF domain (the portion of from position 342 to position 558 of the amino acid sequence of TRAF5), the vertically lined part represents a leucine zipper motif (the portion of from position 261 to position 303 of the amino acid sequence of the TRAF5 molecule), the obliquely lined part represents a Zn finger motif (the portion of from position 111 to position 250 of the amino acid sequence of the TRAF5 molecule), and the horizontally lined part represents a Zn ring finger motif (the portion of from position 45 to position 85 of the amino acid sequence of TRAF5).

Example 2
Investigation of Expression of the TRAF5 Molecule in Tissues

As to which tissue TRAF5 was expressed in was investigated in the following manner:

(1) Tissues were extracted from murine brain, thymus, lung, liver, spleen, heart, stomach, and adrenal gland, and then, respective total RNAs were extracted with RNAZ01B.

(2) Subsequently, employing a Poly(A) quick mRNA isolation kit (available from Stratagene Inc.), Poly(A) RNAs were prepared according to the same protocol as 9 in Example 1.

(3) For these Poly(A) RNAs, the RNA was denatured by heating it in 50% formamide at 65° C. for 5 min, electrophoresed on a 1.5% agarose gel containing 6.6% formamide and transferred to a nitrocellulose membrane (also, a nylon membrane usable).

Figure 2:
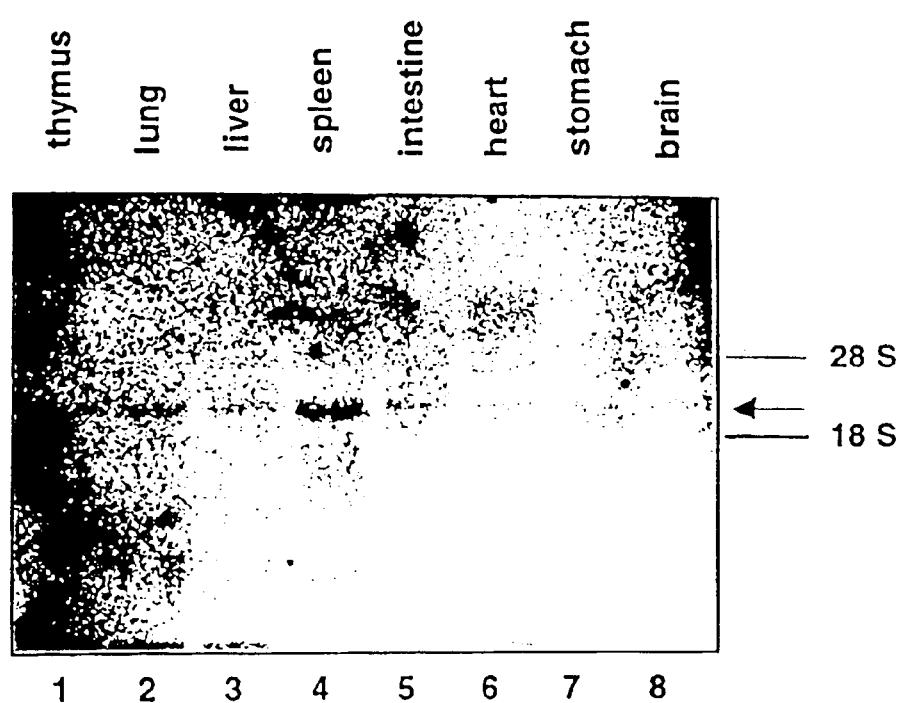
FIG. 2 is a photograph showing the results of a northern blot hybridization analysis of the murine TRAF5 gene in respective tissues, where the arrow indicates the position of a band of the murine TRAF5 gene.

(4) The DNA probe prepared in 10.1 of Example 1 was used as a $^{32}$P-probe. Hybridization manipulations were carried out under the high stringent conditions according to "Molecular Cloning A Laboratory Manual 2nd Edition," p. 7.39–7.52. The results are shown in FIG. 2. "28S" indicates the position of 4.9 kb and "18S" indicates the position of 1.9 kb. mRNA bands were observed at the positions of 2.2 kb (as indicated by the arrow) in all the tissues, thus ascertaining expression of the TRAF5 gene.

Example 3
Screening for TRAF5-Associated Substances

Screening was conducted for any substances among the TNF-R family molecules that associate TRAF5.

(1) As regards TNF-R1, TNF-R2, CD40, and LT-βR among the TNF-R family molecules, a fusion protein with GST was prepared by inserting into the downstream region of glutathione-S-trasnferase (GST), a domain part within the cytoplasm of each TNF-R family molecule.

(2) Employing an In vitro transcription and translation system (TNT available from Promega Inc.), TRAF5 was translated in vitro following its attached manual. Electrophoresis ascertained that the TRAF 5 in vitro translated product was labeled with $^{35}$S-methionine.

(3) Next, the TRAF5 in vitro translated product was mixed with GST and each kind of the fusion proteins prepared in (1).

(4) Subsequently, the mixture was added to a GSH agarose column, and GST and the GST-TNF-R family molecule (which may contain any associated substance with the TRAF5 molecule) were allowed to adsorb to the column.

(5) Then, beads in the GSH agarose column were added to a SDS sample buffer and boiled at 95° C. for 5 min in order to dissociate the TRAF5 molecule that was associating any GST-TNF-R family molecule therefrom.

(6) Then, after the beads were precipitated by centrifugation, the supernatant was subjected to SDS-PAGE. A 10% gel was used as a gel, and after electrophoresis, it was incubated in an Amplify (Registered Trademark, available from Amasham Inc.) for 30 min.

Figure 3:
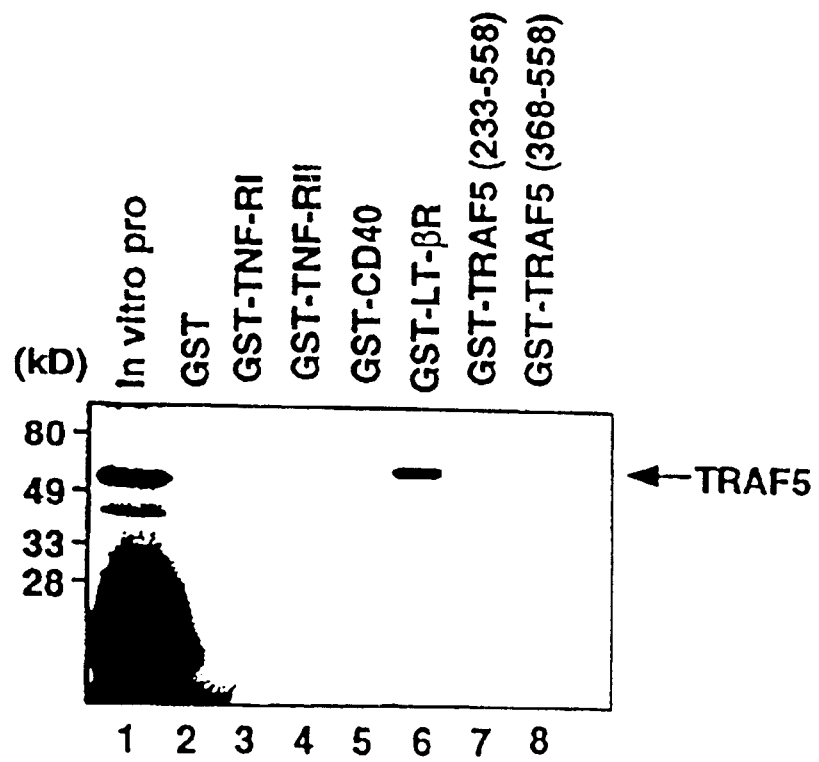
FIG. 3 is a photograph showing the results of SDS-PAGE from screening for any TNF-R family molecules that associate the murine TRAF5 molecule, where the arrow indicates the position of a band of the murine TRAF5 molecule.

(7) Thereafter, the gel was dried and exposed to an X-ray film. The results are shown in FIG. 3. The "In vitro pro" lane represents a lane for the in vitro translated product in FIG. 3. In addition, the name of each kind of the fusion proteins, which was used, is entered in each lane. As is evident from FIG. 3, a band corresponding to the TRAF5 molecule at about 50 kD could be detected in the case of reaction with the GST-fusion protein of LT-βR. In other words, the TRAF5 molecule was found to associate LT-βR.

Example 4
Immunoprecipitation Western Blotting

According to the immunoprecipitation western blotting, association between the TRAF5 molecule and LT-βR was ascertained.

(1) First, the hemagglutinin epitope (HA epitope) of influenza virus was bound to the TRAF5 molecule as a tag in the following manner:

(i) An oligonucleotide corresponding to nine amino acids of the HA epitope was synthesized. Specifically, formula (1) as described below was synthesized as a sense polynucleotide and formula (2) as an antisense polynucleotide by means of a DNA synthesizer.

Formula (1) 5'-AAT TGA TGT ACC CAT AGG ATG TTC CAG ATT ACG CTG ATT TCC-3' (SEQ ID NO: 5)
Formula (2) 5'-TCG AGG AAT TCA GCG TAA TCT GGA ACA TCG TAT GGG TAC ATC-3' (SEQ ID NO: 6)

(ii) These polynucleotides were mixed and annealed at 50° C. for 10 min.

(iii) Next, phosphorylation was carried out using a T4 polynucleotide kinase (available from Promega Inc.).

(iv) This was subcloned into a vector plasmid pMKITneo that had been treated with restriction enzymes-EcoRI and XhoI, the resulting clone was designated pHAKITneo.

(v) The pHAKITneo was treated with EcoRI and the TRAF5 gene that had been amplified by PCR was subcloned into it. As compared to direct introduction of the TRAF5 gene into pMKITneo by EcoRI treatment, reading can be well done in inframe when TRAF5 is introduced into pHAKITneo.

(2) Next, 2.5 μg of the pHAKITneo-TRAF5 gene and pcDNA1-LT-βR (LT-βR-introduced vector) were transiently introduced into COS7 Cell (ATCC CRL-1651) 2×10$^6$ cells, respectively by the DEAE-dextran method (available from Pharmacia Inc.).

(3) After transformants of the COS7 cells were grown for 48 h and the proteins encoded by the introduced genes were allowed to produce, the cells were recovered and dissolved with a cytolytic solution. For the cytolytic solution, a solution containing 0.1% NP-40, 50 mM HEPES (pH 7.4), 250 mM NaCl, 10% glycerol, 2 mM EDTA, 1 mM PMSF, 2μg/ml aprotinin, 2 μg/ml Pepstatin A, and 2 μg/ml leupeptin was used.

(4) The anti-LT-βR antibody was allowed to act on a solution into which these cells had been dissolved and the TRAF5-LT-βR complex was immunoprecipitated.

(i) Preclearing was conducted against the supernatant (1 ml) of the cell-dissolved solution with the aid of Sepharose beads bound to goat IgG. Namely, 100 μl of goat Sepharose beads (equivalent to 50 μl of beads) was added to 1 ml of the supernatant and they were allowed to react at 4° C. for 16 h. Thereafter, the beads were removed by centrifugation at 6,000 rpm for 2 min and any substances bound to the goat IgG in nonspecific manner were thus removed.

(ii) Next, 100 μg of Sepharose beads (equivalent to 50 μl of beads) to which the anti-LT-βR antibody was bound was added to the supernatant and they were allowed to react at 4° C. for 16 h. Thereafter, parts that did not adsorb to the beads were removed by centrifugation, and further, these beads were centrifuged in the cytolytic solution used in (3) twice.

(5) These beads were put into 20 μl of a reductive sample buffer for SDS-PAGE and boiled for 5 min.

(6) Subsequently, electrophoresis was conducted using a concentration-gradient gel for SDS-PAGE (acrylamide gel concentration: 10–20%).

(7) After electrophoresis, the gel was transferred onto a nitrocellulose membrane at 10 V at 4° C. overnight.

(8) To this membrane was added Blockace (available from Dainippon Pharmaceutical Co. Ltd.) and blocking was conducted at room temperature for 1 h.

(9) Next, after the membrane was washed with PBS (pH 7.4) containing 0.05% Tween20 for 10 min, the goat anti-HA antibody (available from Boehringer Inc.) was gadded at 10 μg/ml and it was allowed to react at room temperature for 1 h. It was then washed with Tween PBS for 10 min. These manipulations were repeated three times.

(10) Next, a solution containing peroxidase-labeled goat IgG (available from Caltag Inc.) diluted 1000-fold was added to the membrane and it was allowed to react at room temperature for 1 h. After the reaction, the membrane was washed with Tween PBS three times, and the coloring solution from an ECL kit (available from Amasham Inc.) was added and it was allowed to react for 1 min.

Figure 4:
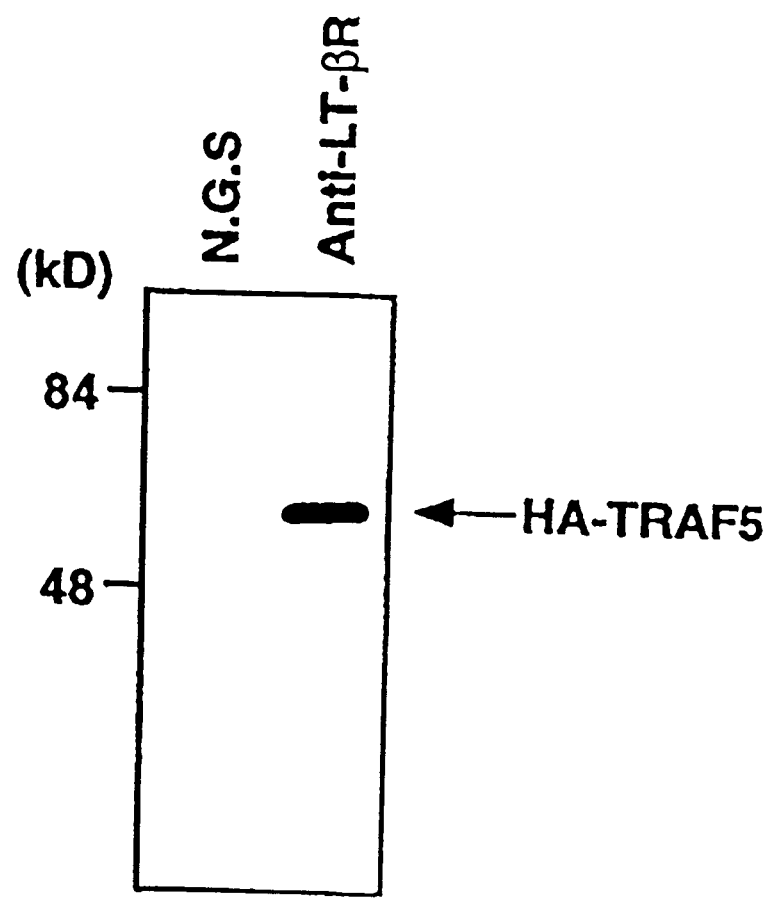
FIG. 4 is a photograph showing the results of immunoprecipitation western blotting by means of a HA epitope, of the associated substance between the murine TRAF5 molecule and LT-βR, where the arrow indicates the position of the murine TRAF5 molecule bound to the HA epitope.

(11) This membrane was exposed to an X-ray film for 20 sec and developed. The result is shown in FIG. 4. "N.G.S." represents a lane for the goat serum and "Anti-LT-βR" represents a lane for the sample obtained by treatment of the immunoprecipitated product with a reductive sample buffer for SDS-PAGE. As is evident from FIG. 4, the band of the HA-TRAF5 molecule at about 60 kD (as indicated by the arrow) can be recognized for the product immunoprecipitated with the anti-LT-βR antibody.

Example 5
Characterization of the TRAF5 Molecule (Investigation of Activation for the DNA-binding of NF-κB)

As to what kind of signals the TRAF5 molecule transmits within the nuclei of cells, investigation was made by studying activation of the DNA-binding of NF-κB.

(1) The three vectors as described below (7.5 μg each) were introduced into 293 Cell 2×10⁶ cells, respectively so that the five expression patterns as described below could be realized. The introduction employed CaPO₄ and the TRAF5 molecule was transiently expressed in the cells.

Vectors Employed:
(i) Vector obtained by insertion of the full-length cDNA of the TRAF5 gene into a pMKITneo vector;
(ii) Vector obtained by insertion of the fragment of from position 233 to position 558 of the TRAF5 gene into a pMKITneo; and
(iii) Vector obtained by insertion of LT-βR into a pMKITneo vector.

Expression Patterns:
(i) pMKITneo Vector only;
(ii) pMKITneo Vector-the full length TRAF5 gene;
(iii) pMKITneo Vector-positions 233–558 of the TRAF5 gene;
(iv) pMKITneo Vector-LT-βR; and
(v) pMKITneo Vector-positions 233–558 of the TRAF5 gene and pMKITneo Vector-LT-βR (the ratio of the former to the latter: 10:1).

(2) Forty-eight hours after the introduction, each 4 μg of a nuclear extract was obtained. (See, "Biomanual Series 5 Methods for Studying Transcription Factors" p. 17–26, Yodo Co. Ltd., 1993.)

(3) Polynucleotides of formulae (3) and (4) as described below, which are the binding sites of NF-κB, were respectively synthesized, and these were made into a double-strand, 5'-end of which was labeled with $^{32}$P by means of Megarabel (Registered Trademark, available from Takara Shuzo Co. Ltd.) to prepare a DNA probe for the detection of NF-κB.

Formula (3) 5' ATCAGGGACTTTCCGCTGGGGACTT 3' (SEQ ID NO: 11)
Formula (4) 5° CGGAAAGTCCCCAGCG-GAAAAGTCCC3' (SEQ ID NO: 12)

(4) The extract of (2) and the probe prepared in (3) were reacted at 37° C. for 30 min.

Figure 5:
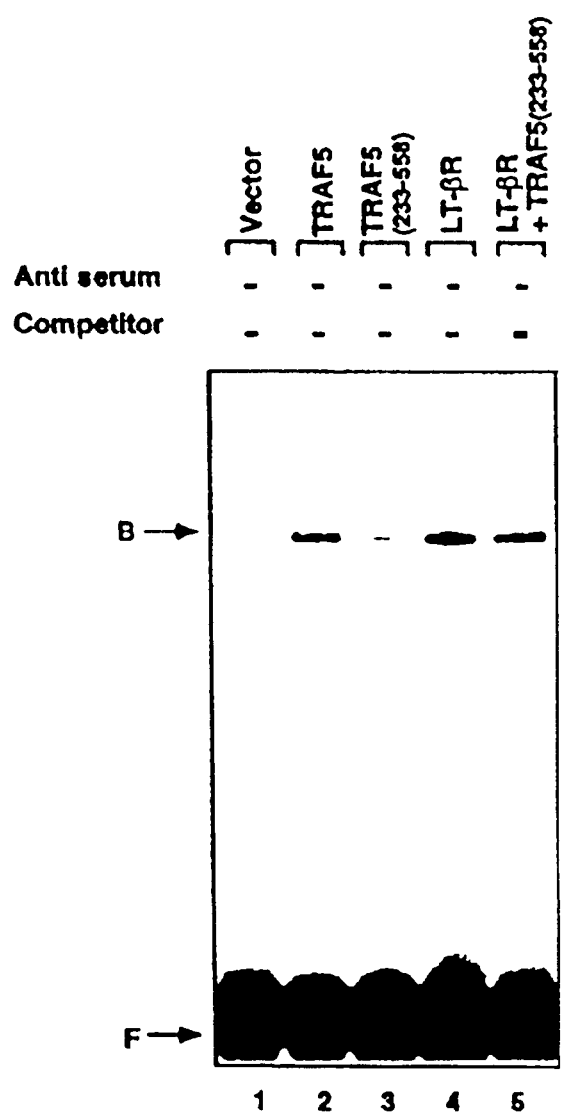
FIG. 5 is a photograph showing the results of an EMSA that illustrates induction of the DNA-binding activity of NF-κB by the murine TRAF5 molecule or the LT-βR molecule, where the band as indicated by "B→" indicates the position of NF-κB and the depth of the band in color indicates the quantity of DNA bound to NF-κB.

(5) After the reaction, electrophoresis was performed in an Electrophoretic Mobility Shift Assay (EMSA) to study the DNA-binding ability of NF-κB. The results are shown in FIG. 5. Lanes 1–5 correspond to the expression patterns (i)–(v) as described above. The band as indicated by "B→" represents the NF-κB bound to the DNA probe for detection. As is evident from FIG. 5, NF-κB is detected by having been bound to the DNA probe if the TRAF5 molecule is expressed. From this, it can be understood that the expression of the TRAF5 molecule induces activation of the DNA-bonding of NF-κB. Although the expression of LT-βR alone also induces the expression of NF-κB, it has been found that if the portion of from position 233 to position 558 of the amino acid sequence of the TRAF5 molecule, which is a deleted protein, is added in an about 10 times excess, this activation can be inhibited. In other words, the DNA-binding activity of NF-κB can be inhibited by the excessive addition of the portion of from position 233 to position 558 of the amino acid sequence of the TRAF5 molecule. This suggests that preparation of the TRAF5 molecule can control the signal transduction.

Example 6
Preparation of Antibodies
1. Preparation of Antigens

The two peptides as described below, which are parts of the TRAF5 molecule, were synthesized using a peptide synthesizer.

Sequence 1: 14 mer peptide comprising Ser Val Lsy Gln Arg Ile Thr Gln Leu Glu Ala Ser Asp (SVKQRITQLEASD (SEQ ID NO:7)) of from position 351 to position 363 of the TRAF5 molecule the N-terminus of which is appended to Cys (C)

Sequence 2: 14 mer peptide comprising Cys Tyr Ser Gly Lys Leu Ile Trp Lys Val Thr Asp Tyr Arg (CYSGKLIWKVTDYR (SEQ ID NO:8)) of from position 401 to position 414 of the TRAF5' molecule 2. Preparation of Polyclonal Antibodies The antibodies were prepared independently against the respective peptides prepared in 1 by following the procedure as described below.

(1) The synthesized peptide (5 mg) was conjugated to 10 mg of KLH (available from Wako Pure Chemicals co. Ltd.) by means of m-maleimidobenzoyl-N-hydroxysuccinimide ester (available from Pierce Inc.) and it was mixed with Freund complete adjuvant (available from Difco Inc.) in the ratio of 1:1 to provide an emulsion.

(2) Rabbits were immunized by intramuscularly injecting the above-mentioned emulsion in an amount of its one sixth per animal.

(3) The same operation was repeated twice every two weeks. Where a polyclonal antibody against a rabbit was to be prepared, blood was collected seven days after the final immunization and serum was separated.

(4) The serum was further salted out with 40% saturated ammonium sulfate and an IgG fraction (polyclonal antibody) was obtained by affinity chromatography using Protein A Sepharose (available from Pharmacia Inc.). The serum (50 ml) produced 270 mg of the polyclonal antibody.

(5) Measurement of the titers for the polyclonal antibodies was carried out by ELISA following the method as described below.

(i) Each of the antigen preparations (peptide of sequence 1 and peptide of sequence 2) 25 μg/ml was fractionally poured to each well of 96-well ELISA plate (Xenobind, available from Xenopore Inc.) at 50 μl per well, and they were allowed to stand at 4° C. overnight.

(ii) The antigen preparation was discarded and Blockace (available from Dainippon Pharmaceuticals Co. Ltd.) diluted 4-fold with distilled water was fractionally poured to each well at 200 μl per well, blocking was performed and it was allowed to stand at room temperature for 2 h.

(iii) The blocking solution was discarded. The polyclonal antibodies diluted 160-, 320-, 640-, 1280-, 2560-, 5120-, and 10240-fold and the serum from a normal nonimmunized rabbit were fractionally poured to eight wells, respectively at 100 μl per well, and they were allowed to stand at room temperature for 1 h.

(iv) The culture supernatant was discarded and the plate was washed with 0.05% Tween20-PBS four times. The biotinylated anti-rabbit IgG antibody (available from Vector Inc.) was fractionally poured to each well at 50 μl per well, and it was allowed to react at room temperature for 1 h.

(v) The plate was washed with 0.05% Tween20-PBS four times. An ABC solution (avidin-biotinylated peroxidase mixture, available from Vector Inc.) was fractionally poured to each well at 50 μl per well, and it was allowed to react for 30 min.

(vi) The plate was washed with 0.05% Tween20-PBS four times. $H_2O_2$-OPD/PCB was fractionally poured to each well at 100 μl per well, and coloring was allowed to occur: A490 values were measured.

Figure 7:
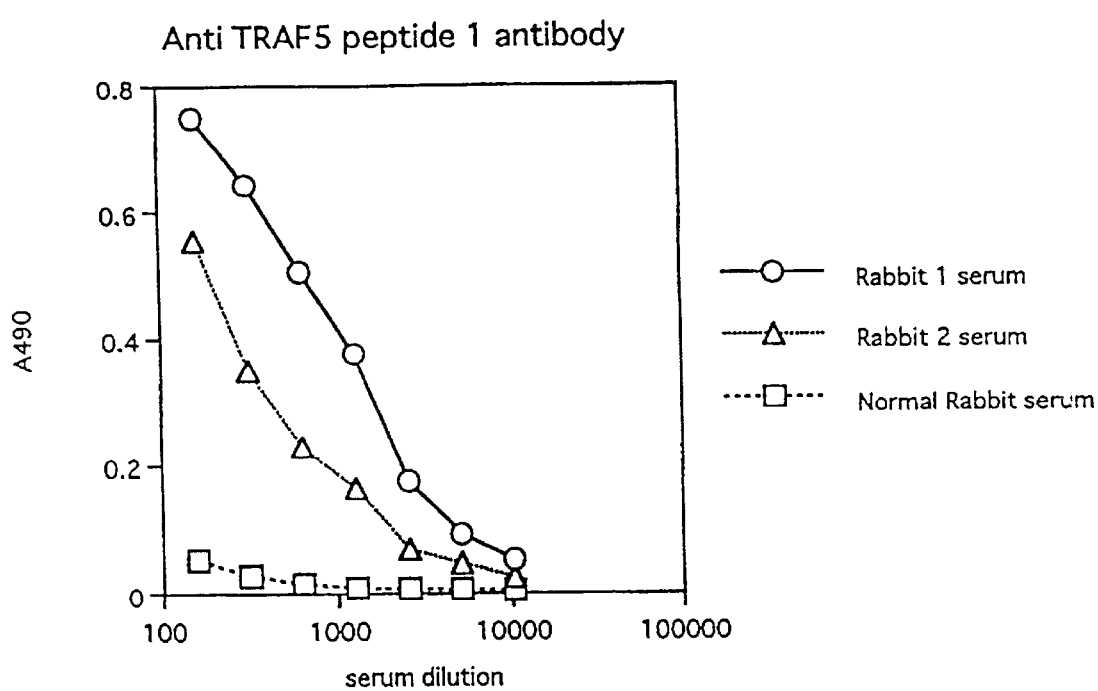
FIG. 7 is a graph showing the results of an ELISA of the polyclonal antibody against the 14 mer peptide (sequence 1 peptide) having Cys (C) appended to the N-terminus of the TRAF5 molecule: Ser Val Lsy Gln Arg Ile Thr Gln Leu Glu Ala Ser Asp (SVKQRITQLEASD) (SEQ ID NO:7), i.e., positions 351–363.
Figure 8:
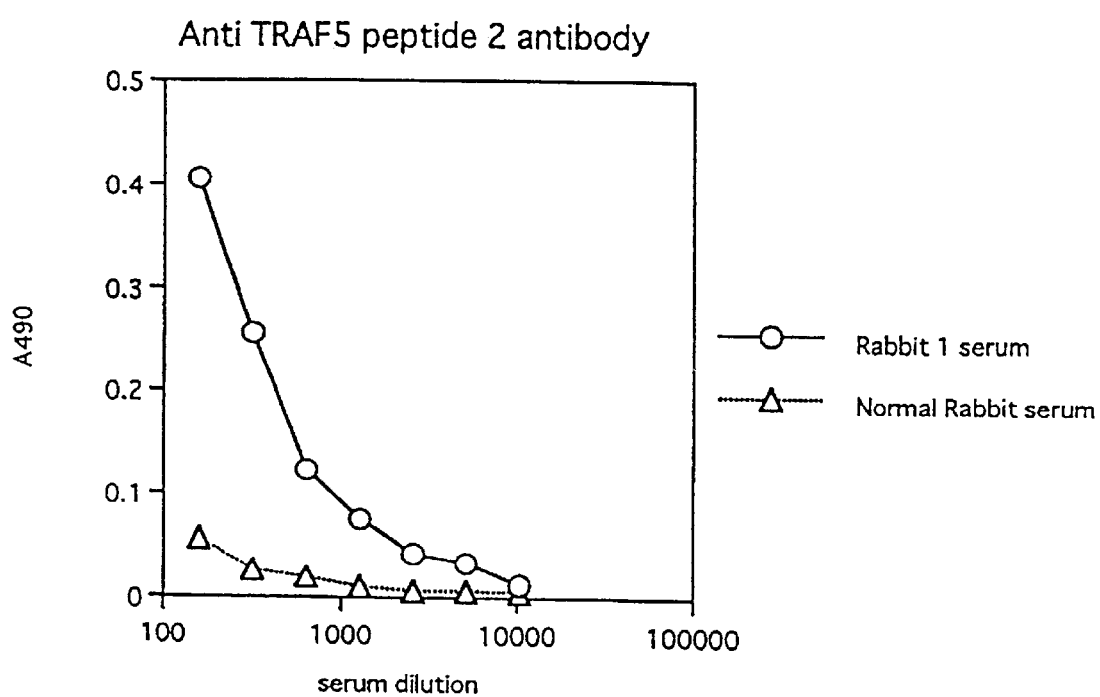
FIG. 8 is a graph showing the results of an ELISA of the polyclonal antibody against the 14 mer peptide (Sequence 2 peptide) having Cys Tyr Ser Gly Lys Leu Ile Trp Lys Val Thr Asp Tyr Arg (CYSGKLIWKVTDYR) (SEQ ID NO:8): positions 401–414 of the murine TRAF5 molecule.

These results are shown in FIGS. 7 and 8. FIG. 7 is a graph showing the results of an ELISA for the polyclonal antibody against the peptide of sequence 1. FIG. 8 is a graph showing the results of an ELISA for the polyclonal antibody against the peptide of sequence 2. In the figures, the axis of abscissas represents concentrations of the added polyclonal antibody and the axis of ordinates represents A490 values. "Peptide of Sequence 1" represents the results of an ELISA for the polyclonal antibody obtained by immunization of two rabbits. From the fact that A490 values are raised by addition of the antibody, it can be understood that the antibody has reacted with the antigen.

Example 7
Cloning of the Human TRAF5 Gene
1. Preparation of cDNA Library

The preparation of a cDNA library was carried out by a method similar to 9 of Example 1. However, HAT109 Cell into which the gene of human HLTV-1 had been introduced (provided by Dr. Yoshida at Medical Sciences Research Institute of the University of Tokyo) and a λgt11 cDNA Library kit (available from Stratagene Inc.) were employed, respectively instead of murine mocyte cell strain J777A.1 cells and the Uni-ZAP cDNA Library kit (Registered Trademark, available from Stratagene Inc.).

2. Screening for cDNA cDNA for the portion of from position 1646 to position 1966 of the base sequence set forth in SEQ ID No. 2 of the Sequence Listing was labeled with [$\alpha^{32}$P]dCTP using a Rediprime kit (available from Amasham Inc.). The cDNA library prepared in 1 was screened according to the plaque hybridization method (See, "Cell Experimental Protocols," p. 57–65), using this cDNA as a probe. Nineteen positive clones resulted. DNA sequencing was conducted on all of these clones and the base sequence of each clone was determined. This result revealed that the 19 clones were the fragments of one full-length gene. From these fragments, the base sequence of the human TRAF5 gene was determined. The base sequence is set forth in SEQ ID No. 4 of the Sequence Listing. The amino acid sequence of human TRAF5 is also set forth in SEQ ID No. 3 of the Sequence Listing.

Transformed E. coli into which the longest gene (which contains positions 421–1860 of SEQ ID No. 4 of the Sequence Listing) out of the 19 clones had been introduced was deposited on Feb. 14, 1996 in the National Institute of Bioscience and Human-Technology, Agency of Industrial Science and Technology, Ministry of International Trade and Industry locating at 1-1-3 Higashi, Tsukuba, Ibaragi, 305 Japan (Accession No: FERM BP-5821). Further, concerning the portions that do not reached the full length, information was obtained from other clones.

When human TRAF5 is compared to the structure of murine TRAF5 molecule with regard to the positions of respective domains, it is recognized that the TRAF domain is positions 342–557, the leucine zipper motif is positions 261–303, the Zn finger motif is positions 111–250, and the ring finger motif is positions 45–85.

Example 8
Cross-Reaction of Antibodies

The reactivity of the anti-murine TRAF5 antibody prepared in Example 6 was investigated.

1. Dissolution of Cells

First, for BJAB (Burkitt's lymphoma), HEK293 (cell strain derived from human fetus), ME180 (cervical carcinoma) and FDC-1 (follicular dendritic cell), the cells were dissolved after their recovery in the following manner. With respect to each, $1 \times 10^6$ cells were used. The cytolytic preparation contains 50 mM Tris-HCl, 150 mM NaCl, 1% NP-40, 50 mM iodoacetamide, 2 mM $MgCl_2$, 2 mM $CaCl_2$, 0.1% $NaN_3$, 1 mM EGTA, 1 mM EDTA, 1 mM $Na_3VO_4$, and 1 mM NaF. This cytolytic preparation (100 μl) was added to pellets of the respective cells and stirred thoroughly to dissolve the cells.

After allowing to stand on ice for 60 min, centrifugation was conducted at 15,000 rpm for 10 min to recover the supernatant.

2. Removal of Nonspecific Binding Proteins

To the recovered supernatant was added 50 μl of beads in which IgG (1 mg) of a nonimmunized rabbit was bound to CNBr-activated Sepharose beads (available from Pharmacia Inc.). After reaction at 4° C. overnight, centrifugation of the supernatant was conducted at 15,000 rpm for 5 min to remove nonspecific binding proteins.

3. Electrophoresis

The solution obtained in 2, 10 μl, was mixed with an equal amount of a SDS-PAGE sample buffer and 1 μl of 2-mercaptoethanol, heat treatment at 95° C. for 5 min was carried out, and then, it was electrophoresed on a 5–20% gradient gel.

4. Membrane Transfer

After electrophoresis, the gel was transferred onto a nitrocellulose membrane with the aid of a Trans Blot System (Marisol Inc.).

5. Blocking

The nitrocellulose membrane was immersed in Blockace (available from Dainippon Pharmaceuticals Inc.) and allowed to stand for 1 h to effect blocking. Thereafter, it was twice washed with 0.05% Tween20/PBS for 5 min.

6. Antigen-Antibody Reaction

After the anti-murine TRAF5 antibody was diluted with PBS to 1 µl/ml, it was added to the membrane and allowed to react at room temperature for 2 h. Thereafter, it was three times washed with 0.05% Tween20/PBS for 5 min.

7. Coloring Reaction

Next, a solution containing peroxidase-labeled anti-rabbit IgG (available from Caltag Inc.) that was diluted with PBS 1000-fold was added to the nitrocellulose membrane and it was allowed to react at room temperature for 1 h. Thereafter, the membrane was washed three times with 0.05% Tween20/PBS for 5 min.

Figure 9:
FIG. 9 is a photograph of western blotting showing expression of the human TRAF5 molecule in respective cell strains, where the arrow indicates the position of a band of the human TRAF5 molecule.

Next, 5 ml of the coloring solution from an ECL kit (available from Amasham Inc.) was added to the membrane and it was further allowed to react for 1 min. Subsequently, this nitrocellulose membrane was exposed to an X-ray film for 20 sec, the film was developed, and then, a photograph was taken. The result is shown in FIG. 9. In FIG. 9, the band of the TRAF5 molecule is observed at the position of about 65 kD in FDC-1 cells. From this, it has become apparent that the anti-murine TRAF5 antibody obtained in Example 4 also cross-reacts the human TRAF5 molecule.

Example 9
Screening (2) for TRAF-Associated Substances

Figure 10:
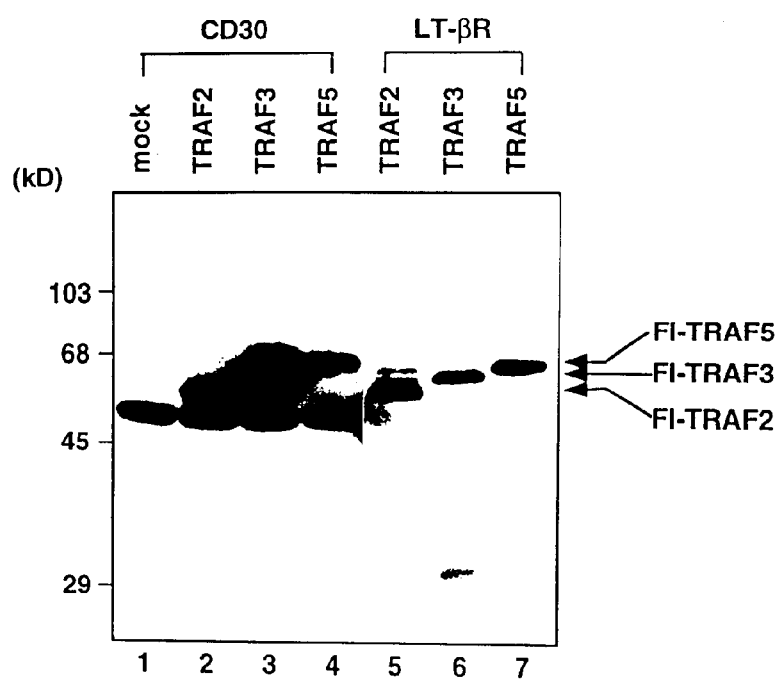
FIG. 10 is a photograph showing that CD30 or LT-βR associates the murine TRAF5 molecule or the murine TRAF2 molecule or the murine TRAF3 molecule, where the arrow indicates the position of the band of the murine TRAF2 molecule, the murine TRAF3 molecule or the murine TRAF5 molecule.

Similarly to the method of Example 3, association between TRAF5 and CD30 was investigated. Also, with respect to TRAF2 and TRAF3, their association with CD30 and LT-βR was investigated in like manner. The results are shown in FIG. 10. As is evident from the figure, it is understood that TRAF5 associates CD30 and that both of TRAF2 and TRAF3 associate either of CD30 and LT-βR. In addition, in FIG. 10 "mock" represents the cell into which a vector plasmid having no insertion was introduced.

Concerning TRAF1, TRAF2, TRAF3, TRAF4, and TRAF5, Table 1 summarizes their functions and structural characteristics obtainable from the combination of the already-known findings and the results from Examples 3 and 5. In the table, "+" means "having the characteristics," "−" means "not having the characteristics," and "N.D." means "can not be determined either way."

TABLE 1

|  | TRAF1 | TRAF2 | TRAF3 | TRAF4 | TRAF5 |
|---|---|---|---|---|---|
| association with TNFR-2 | + | + | + | N.D. | − |
| association with CD40 | + | N.D | + | N.D. | − |
| association with LT-βR | N.D. | + | + | N.D. | + |
| association with CD30 | N.D. | + | + | N.D. | + |

TABLE 1-continued

|  | TRAF1 | TRAF2 | TRAF3 | TRAF4 | TRAF5 |
|---|---|---|---|---|---|
| the ability to induce activation of NF-κB | − | + | − | − | + |
| having leucine zipper motif | − | − | + | − | + |
| having coiled coil structure | + | + | + | + | + |

Industrial Applicability

The TRAF family molecules of this invention are useful to elucidate the functions of the TNF-R family molecules. The TNF-R family molecules and TNF are a group of important molecules that are the trigger for causing differentiation, proliferation and necrosis within the cells. Thus, if the TRAF family molecules are used to elucidate the foregoing phenomena, it will presumably lead to elucidation of the mechanisms for differentiation of the immune system, cancer and apotosis.

The TRAF family molecules of this invention are also useful for elucidation of the signal transduction from LT-βR and as immunomodulators for the signals of LT-βR.

The antibodies of this invention enable the detection of the TRAF family molecules existing in body fluids and tissues. The antibodies also enable the preparation of antibody columns useful to purify the TRAF family molecules of this invention, as well as enable the detection of the TRAF family molecules in respective fractions.

Active fragments of the antibody of this invention enable the preparation of chimera antibodies.

Polynucleotide probes for research and diagnosis that aim at investigating the presence of the genes encoding the TRAF family molecules and their expression state in tissues and cells are provided by the genes encoding the TRAF family molecules of this invention, the polynucleotides comprising the base sequences of the antisense chains of the genes, parts thereof and derivatives thereof.

It is also possible to regulate the expression of TRAF family molecules by the genes encoding TRAF family molecules of this invention, the polynucleotide comprising the base sequences of the antisense chains of the gene, parts thereof and derivatives thereof. In other words, the TRAF family molecules and derivatives thereof provide therapeutic agents for disorders of the signal transduction system involving the TRAF family molecules, as well as for the disorders involving the LT-βR- and CD30-mediated signals. That is, it is possible to develop antisense drugs based on the polynucleotides and derivatives thereof.

What is claimed is:

1. A purified TRAF family protein comprising the amino acid sequence set forth in SEQ ID NO: 1 or SEQ ID NO: 3, and which binds to and associates lymphotoxin-β receptors (LT-βR) and CD30; induces the DNA-binding activity of a DNA binding protein; does not associated CD40 or TNF-R2; and has a leucine zipper motif or a coiled coil structure.

2. The purified TRAF family protein according to claim 1, wherein said molecule is a protein encoded by a DNA molecule having the nucleotide sequence set forth in SEQ ID NO: 2.

* * * * *

SEQUENCE LISTING

<160> NUMBER OF SEQ ID NOS: 16

<210> SEQ ID NO 1
<211> LENGTH: 558
<212> TYPE: PRT
<213> ORGANISM: Mus sp.

<400> SEQUENCE: 1

Met Ala His Ser Glu Glu Gln Ala Ala Val Pro Cys Ala Phe Ile Arg
 1               5                  10                  15

Gln Asn Ser Gly Asn Ser Ile Ser Leu Asp Phe Glu Pro Asp Thr Glu
            20                  25                  30

```
Tyr Gln Phe Val Glu Gln Leu Glu Glu Arg Tyr Lys Cys Ala Phe Cys
        35                  40                  45

His Ser Val Leu His Asn Pro His Gln Thr Gly Cys Gly His Arg Phe
    50                  55                  60

Cys Gln Gln Cys Ile Arg Ser Leu Arg Glu Leu Asn Ser Val Pro Ile
65              70                  75                      80

Cys Pro Val Asp Lys Glu Val Ile Lys Pro Gln Glu Val Phe Lys Asp
                85                  90                  95

Asn Cys Cys Lys Arg Glu Val Leu Asn Leu His Val Tyr Cys Lys Asn
            100                 105                 110

Ala Pro Gly Cys Asn Ala Arg Ile Ile Leu Gly Arg Phe Gln Asp His
        115                 120                 125

Leu Gln His Cys Ser Phe Gln Ala Val Pro Cys Pro Asn Glu Ser Cys
    130                 135                 140

Arg Glu Ala Met Leu Arg Lys Asp Val Lys Glu His Leu Ser Ala Tyr
145                 150                 155                 160

Cys Arg Phe Arg Glu Glu Lys Cys Leu Tyr Cys Lys Arg Asp Ile Val
                165                 170                 175

Val Thr Asn Leu Gln Asp His Glu Glu Asn Ser Cys Pro Ala Tyr Pro
            180                 185                 190

Val Ser Cys Pro Asn Arg Cys Val Gln Thr Ile Pro Arg Ala Arg Val
        195                 200                 205

Asn Glu His Leu Thr Val Cys Pro Glu Ala Glu Gln Asp Cys Pro Phe
    210                 215                 220

Lys His Tyr Gly Cys Thr Val Lys Gly Lys Arg Gly Asn Leu Leu Glu
225                 230                 235                 240

His Glu Arg Ala Ala Leu Gln Asp His Met Leu Leu Val Leu Glu Lys
                245                 250                 255

Asn Tyr Gln Leu Glu Gln Arg Ile Ser Asp Leu Tyr Gln Ser Leu Glu
            260                 265                 270

Gln Lys Glu Ser Lys Ile Gln Gln Leu Ala Glu Thr Val Lys Lys Phe
        275                 280                 285

Glu Lys Glu Leu Lys Gln Phe Thr Gln Met Phe Gly Arg Asn Gly Thr
290                 295                 300

Phe Leu Ser Asn Val Gln Ala Leu Thr Ser His Thr Asp Lys Ser Ala
305                 310                 315                 320

Trp Leu Glu Ala Gln Val Arg His Leu Leu Gln Ile Val Asn Gln Gln
                325                 330                 335

Pro Ser Arg Leu Asp Leu Arg Ser Leu Val Asp Ala Val Asp Ser Val
            340                 345                 350

Lys Gln Arg Ile Thr Gln Leu Glu Ala Ser Asp Gln Arg Leu Val Leu
        355                 360                 365

Leu Glu Gly Glu Thr Ser Lys His Asp Ala His Ile Asn Ile His Lys
    370                 375                 380

Ala Gln Leu Asn Lys Asn Glu Glu Arg Phe Lys Gln Leu Glu Gly Ala
385                 390                 395                 400

Cys Tyr Ser Gly Lys Leu Ile Trp Lys Val Thr Asp Tyr Arg Val Lys
                405                 410                 415

Lys Arg Glu Ala Val Glu Gly His Thr Val Ser Val Phe Ser Gln Pro
            420                 425                 430

Phe Tyr Thr Ser Arg Cys Gly Tyr Arg Leu Cys Ala Arg Ala Tyr Leu
        435                 440                 445

Asn Gly Asp Gly Ser Gly Lys Gly Thr His Leu Ser Leu Tyr Phe Val
```

|     | 450 |     |     |     | 455 |     |     |     | 460 |     |     |
| --- | --- | --- | --- | --- | --- | --- | --- | --- | --- | --- | --- |

Val Met Arg Gly Glu Phe Asp Ser Leu Leu Gln Trp Pro Phe Arg Gln
465             470                 475                 480

Arg Val Thr Leu Met Leu Leu Asp Gln Ser Gly Lys Lys Asn His Ile
                485                 490                 495

Val Glu Thr Phe Lys Ala Asp Pro Asn Ser Ser Ser Phe Lys Arg Pro
            500                 505                 510

Asp Gly Glu Met Asn Ile Ala Ser Gly Cys Pro Arg Phe Val Ser His
        515                 520                 525

Ser Thr Leu Glu Asn Ser Lys Asn Thr Tyr Ile Lys Asp Asp Thr Leu
    530                 535                 540

Phe Leu Lys Val Ala Val Asp Leu Thr Asp Leu Glu Asp Leu
545             550                 555

<210> SEQ ID NO 2
<211> LENGTH: 2254
<212> TYPE: DNA
<213> ORGANISM: Mus sp.

<400> SEQUENCE: 2

```
ggaacgagtg tcgaggcgaa gcagcctagt gcccgccgcc gtagggcgcc agcggagctc    60
cgcgagcccc gcaagtggcg aagtccgggt gagctaaccg tcccggctcc tcagaaaccg   120
aaagcaactc aggtggtgga gccggaggcg tgtgtggtag cgggcgaact gaggcgacgc   180
gggacacccg cgcccggccg agggcacttt tgcaagactt gtgagcacag cccgttaacg   240
tgagcttaat gccagggtct cgagcctgcg ccggtgctat agcgcgtgct cgattggaaa   300
cagaacccga ctctgcagaa gaatggctca ttcggaggag caagcggctg tcccctgcgc   360
cttcatccgc cagaactctg caactcaat ttccttggac tttgagcccg acaccgagta   420
ccagtttgtg gagcagctgg aagaacgcta caaatgtgcc ttctgccact ccgtgcttca   480
caacccccac cagaccggct gcgggcaccg cttctgccag cagtgcatcc ggtctctgag   540
agaattgaac tcgtgccga tctgcccggt agacaaggag gtcatcaagc tcaggaggt   600
gttcaaagac aactgctgca aaagagaagt tctcaattta cacgtctact gcaaaaacgc   660
ccccgggtgc aatgccagga ttattctggg acgattccag gaccaccttc agcactgttc   720
cttccaagcc gtgccctgcc ctaacgagag ctgccgggaa gccatgctcc ggaaagacgt   780
gaaagagcac ctgagcgcat actgccggt ccgagaggaa aagtgccttt actgcaaaag   840
ggacatagtg gtgaccaacc tgcaggatca tgaggaaaac tcgtgtcctg cgtacccagt   900
gtcttgtccc aacaggtgtg tgcagactat tccaagagct agggtgaatg aacaccttac   960
tgtatgtcct gaggctgagc aagactgtcc ctttaagcac tatggctgca ctgtcaaggg   1020
taagcggggg aacttgctgg agcatgagcg ggcagccctg caggaccaca tgcttctggt   1080
tttagagaag aactaccaac tagaacagcg gatctctgat ttatatcaga gtctcgaaca   1140
gaaggaaagc aagatccagc agctggcaga accgtgaag aagttcgaaa aggagcttaa   1200
gcagttcaca cagatgtttg cagaaatgg aactttcctc tcaaatgtcc aggctctcac   1260
cagtcacacg gacaagtcag cttggctgga agcgcaggtg cggcatctgc tacaaatagt   1320
taaccagcag ccaagtcgac ttgatctgag gtctttggtg gatgcggttg acagcgtgaa   1380
acagaggatc acccagctgg aagccagtga ccagagatta gttctttag aggggagac   1440
cagcaagcac gacgcacaca ttaatatcca caaagcacag ctgaataaga acgaagagcg   1500
gtttaagcag ctggagggcg cctgctacag tggcaagctc atctggaagg tgacagatta   1560
```

-continued

```
cagggtgaag aagagggagg ccgtggaggg gcacacagtg tccgtcttca gccagccttt    1620
ctacaccagc cgctgcggct accggctctg tgccagggcg tacctgaacg ggacgggtc     1680 ggggaaggga acgcacctgt ccctgtactt tgtggtgatg cgcggtgagt ttgactcgcg    1740
gctgcagtgg ccgttcaggc agaggtgac cctgatgctt ttggaccaga gcggcaagaa     1800
gaaccatatt gtggagacct tcaaagctga ccccaacagc agcagcttca aaggccaga     1860 tggcgagatg aacattgcct ctggctgtcc ccgctttgtg tcgcactcta ctctggagaa    1920
ctccaagaac acctacatta agacgacac actgttcttg aaagtggccg tggatttaac     1980
tgacttggag gatctgtagt gttacctgat aaggaaactt ctcagcacag gaaaaggtgt    2040
ggctgtccct tgggctcagc cctctggact gagcaggctc ttgttcttgt cttcctgcct    2100
ccgatgtctg atgtgtcatc tttttatctt ggatccttcc ctggtttgaa actttaaact    2160
cttgaaatat tgctgttatt tatattttg tatcttccaa aaaattataa taatttgaca     2220
acccaaaaaa aaaaaaaaaa aaaaaaaaaa aaaa                                2254
```

<210> SEQ ID NO 3
<211> LENGTH: 557
<212> TYPE: PRT
<213> ORGANISM: Homo sapiens

<400> SEQUENCE: 3

```
Met Ala Tyr Ser Glu Glu His Lys Gly Met Pro Cys Gly Phe Ile Arg
 1               5                  10                  15

Gln Asn Ser Gly Asn Ser Ile Ser Leu Asp Phe Glu Pro Ser Ile Glu
            20                  25                  30

Tyr Gln Phe Val Glu Arg Leu Glu Arg Tyr Lys Cys Ala Phe Cys
        35                  40                  45

His Ser Val Leu His Asn Pro His Gln Thr Gly Cys Gly His Arg Phe
    50                  55                  60

Cys Gln His Cys Ile Leu Ser Leu Arg Glu Leu Asn Thr Val Pro Ile
65                  70                  75                  80

Cys Pro Val Asp Lys Glu Val Ile Lys Ser Gln Glu Val Phe Lys Asp
                85                  90                  95

Asn Cys Cys Lys Arg Glu Val Leu Asn Leu Tyr Val Tyr Cys Ser Asn
            100                 105                 110

Ala Pro Gly Cys Asn Ala Lys Val Ile Leu Gly Arg Tyr Gln Asp His
        115                 120                 125

Leu Gln Gln Cys Leu Phe Gln Pro Val Gln Cys Ser Asn Glu Lys Cys
    130                 135                 140

Arg Glu Pro Val Leu Arg Lys Asp Leu Lys Glu His Leu Ser Ala Ser
145                 150                 155                 160

Cys Gln Phe Arg Lys Glu Lys Cys Leu Tyr Cys Lys Lys Asp Val Val
                165                 170                 175

Val Ile Asn Leu Gln Asn His Glu Glu Asn Leu Cys Pro Glu Tyr Pro
            180                 185                 190

Val Phe Cys Pro Asn Asn Cys Ala Lys Ile Ile Leu Lys Thr Glu Val
        195                 200                 205

Asp Glu His Leu Ala Val Cys Pro Glu Ala Glu Gln Asp Cys Pro Phe
    210                 215                 220

Lys His Tyr Gly Cys Ala Val Thr Asp Lys Arg Arg Asn Leu Gln Gln
225                 230                 235                 240

His Glu His Ser Ala Leu Arg Glu His Met Arg Leu Val Leu Glu Lys
```

```
            245                 250                 255
Asn Val Gln Leu Glu Gln Ile Ser Asp Leu His Lys Ser Leu Glu
            260                 265                 270
Gln Lys Glu Ser Lys Ile Gln Gln Leu Ala Glu Thr Ile Lys Lys Leu
            275                 280                 285
Glu Lys Glu Phe Lys Gln Phe Ala Gln Leu Phe Gly Lys Asn Gly Ser
            290                 295                 300
Phe Leu Pro Asn Ile Gln Val Phe Ala Ser His Ile Asp Lys Ser Ala
305                 310                 315                 320
Trp Leu Glu Ala Gln Val His Gln Leu Leu Gln Met Val Asn Gln Gln
            325                 330                 335
Gln Asn Lys Phe Asp Leu Arg Pro Leu Met Glu Ala Val Asp Thr Val
            340                 345                 350
Lys Gln Lys Ile Thr Leu Leu Glu Asn Asn Asp Gln Arg Leu Ala Val
            355                 360                 365
Leu Glu Glu Glu Thr Asn Lys His Asp Thr His Ile Asn Ile His Lys
            370                 375                 380
Ala Gln Leu Ser Lys Asn Glu Glu Arg Phe Lys Leu Leu Glu Gly Thr
385                 390                 395                 400
Cys Tyr Asn Gly Lys Leu Ile Trp Lys Val Thr Asp Tyr Lys Met Lys
            405                 410                 415
Lys Arg Glu Ala Val Asp Gly His Thr Val Ser Ile Phe Ser Gln Ser
            420                 425                 430
Phe Tyr Thr Ser Arg Cys Gly Tyr Arg Leu Cys Ala Arg Ala Tyr Leu
            435                 440                 445
Asn Gly Asp Gly Ser Gly Arg Gly Ser His Leu Ser Leu Tyr Phe Val
            450                 455                 460
Val Met Arg Gly Glu Phe Asp Ser Leu Leu Gln Trp Pro Phe Arg Gln
465                 470                 475                 480
Arg Val Thr Leu Met Leu Leu Asp Gln Ser Gly Lys Lys Asn Ile Met
            485                 490                 495
Glu Thr Phe Lys Pro Asp Pro Asn Ser Ser Ser Phe Lys Arg Pro Asp
            500                 505                 510
Gly Glu Met Asn Ile Ala Ser Gly Cys Pro Arg Phe Val Ala His Ser
            515                 520                 525
Val Leu Glu Asn Ala Lys Asn Ala Tyr Ile Lys Asp Asp Thr Leu Phe
            530                 535                 540
Leu Lys Val Ala Val Asp Leu Thr Asp Leu Glu Asp Leu
545                 550                 555

<210> SEQ ID NO 4
<211> LENGTH: 2894
<212> TYPE: DNA
<213> ORGANISM: Homo sapiens

<400> SEQUENCE: 4
cttgttgtgc ctgacggaag agcaagacgg ccacaattca gacgcacgtg agggaaatca      60
gatgactgga cttgtagata ctaacggttc tgaagcggaa tggcttattc agaagagcat     120
aaaggtatgc cctgtggttt catccgccag aattccggca actccatttc cttgactttt     180
gagcccagta tagagtacca gtttgtggag cggttggaag agcgctacaa atgtgccttc     240
tgccactcgg tgcttcacaa cccccaccag acaggatgtg ggcaccgctt ctgccagcac     300
tgcatcctgt ccctgagaga attaaacaca gtgccaatct gccctgtaga taaagaggtc     360
```

-continued

| | |
|---|---|
| atcaaatctc aggaggtttt taaagacaat tgttgcaaaa gagaagtcct caacttatat | 420 |
| gtatattgca gcaatgctcc tggatgtaat gccaaggtta ttctgggccg gtaccaggat | 480 |
| caccttcagc agtgcttatt tcaacctgtg cagtgttcta atgagaagtg ccgggagcca | 540 |
| gtcctacgga aagacctgaa agagcatttg agtgcgtcct gtcagtttcg aaaggaaaaa | 600 |
| tgcctttatt gcaaaaagga tgtggtagtc atcaatctac agaatcatga ggaaaacttg | 660 |
| tgtcctgaat acccagtatt ttgtcccaac aattgtgcga agattattct aaaaactgag | 720 |
| gtagatgaac acctggctgt atgtcctgaa gctgagcaag actgtccttt taagcactat | 780 |
| ggctgtgctg taacggataa acggaggaac ctgcagcaac atgagcattc agccttacgg | 840 |
| gagcacatgc gtttggtttt agaaaagaat gtccaattag aagaacagat ttctgactta | 900 |
| cacaagagcc tagaacagaa agaaagtaaa atccagcagc tagcagaaac tataaagaaa | 960 |
| cttgaaaagg agttcaagca gtttgcacag ttgtttggca aaaatggaag cttcctccca | 1020 |
| aacatccagg ttttttgccag tcacattgac aagtcagctt ggctagaagc tcaagtgcat | 1080 |
| caattattac aaatggttaa ccagcaacaa ataaatttg acctgagacc tttgatggaa | 1140 |
| gcagttgata cagtgaaaca gaaaattacc ctgctagaaa acaatgatca agattagcc | 1200 |
| gttttagaag aggaaactaa caaacatgat acccacatta atattcataa agcacagctg | 1260 |
| agtaaaaatg aagagcgatt taaactgctg gagggtactt gctataatgg aaagctcatt | 1320 |
| tggaaggtga cagattacaa gatgaagaag agagaggcgg tggatgggca cacagtgtcc | 1380 |
| atcttcagcc agtccttcta caccagccgc tgtggctacc ggctctgtgc tagagcatac | 1440 |
| ctgaatgggg atgggtcagg aggggggtca cacctgtccc tatactttgt ggtcatgcga | 1500 |
| ggagagtttg actcactgtt gcagtggcca ttcaggcaga gggtgaccct gatgcttctg | 1560 |
| gaccagagtg gcaaaagaa cattatggag accttcaaac ctgaccccaa tagcagcagc | 1620 |
| tttaaaagac ctgatgggga gatgaacatt gcatctggct gtccccgctt tgtggctcat | 1680 |
| tctgttttgg agaatgccaa gaacgcctac attaaagatg acactctgtt cttgaaagtg | 1740 |
| gccgtggact taactgacct ggaggatctc tagtcactgt tatggggtga taagaggact | 1800 |
| tcttggggcc agaactggag gagagcacat ttgattatca tattgacctg gatttagact | 1860 |
| caaagcacat ttgtatttgc ctttttcctt aacgtttgaa gtcagtttaa aacttctgaa | 1920 |
| gtgctgtctt tttacatttt actctgtccc agtttgaaac ttaaaactct tagaatattc | 1980 |
| tcttattatt tatattttta tatttcttga aagatggtaa gtttcttgaa gttttttgggg | 2040 |
| cgtttctctt ttactggtgc ttagcgcagt gtctcgggca ctctaaatat tgagtgttat | 2100 |
| ggaggacaca gaggtagcag aatcccagtt gaaaatgttt tgatatttta ttgtttggcc | 2160 |
| tattgattct agacctggcc ttaagtctgc aaaagccatc tttataaggt aggctgttcc | 2220 |
| agttaagtag tgggtgatgt agttacaaag ataatatgct cagtttggac cttttttttca | 2280 |
| gttaaatgct aaatatatga aaattactat acctctaagt attttcatga aattcaccag | 2340 |
| cagtttgcaa gcacagtttt gcaaggctgc ataagaactg gtgaatgggg taagcatttt | 2400 |
| cattcttcct gctgaagtaa agcagaaagt actgcatagt atatgagata tagccagcta | 2460 |
| gctaaagttc agattttgtt aggttcaacc ctatgaaaaa actattttc ataggtcaaa | 2520 |
| aatggtaaaa aattagcagt ttcataagat tcaaccaaat aaatatatat atacacacac | 2580 |
| acatacatat acacctatat atgtgtgtat acaaacagtt cgaatgtatt ttggtgacag | 2640 |
| taataaatca atgtgaggat ggatagaatt tagtatatga tagagaaaat gtcataaatg | 2700 |
| gataaaagga atttacaact tgaggagaaa acctttacaa tttcctatgg gtgtcagaag | 2760 |

```
tactctcagc gaaaactgat ggctaaaaca gtatctacta ttctctgata acttttttc      2820 tgagacagag tttcattgtc acccaggctg gagtacagtg gcatgatctc agctcactgc      2880
aaactctgcc tccc                                                        2894
```

```
<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 5
aattgatgta cccataggat gttccagatt acgctgaatt cc                         42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 6
tcgaggaatt cagcgtaatc tggaacatcg tatgggtaca tc                         42

<210> SEQ ID NO 7
<211> LENGTH: 13
<212> TYPE: PRT
<213> ORGANISM: Mus sp.

<400> SEQUENCE: 7

Ser Val Lys Gln Arg Ile Thr Gln Leu Glu Ala Ser Asp
 1               5                  10

<210> SEQ ID NO 8
<211> LENGTH: 14
<212> TYPE: PRT
<213> ORGANISM: Mus sp.

<400> SEQUENCE: 8

Cys Tyr Ser Gly Lys Leu Ile Trp Lys Val Thr Asp Tyr Arg
 1               5                  10

<210> SEQ ID NO 9
<211> LENGTH: 6
<212> TYPE: PRT
<213> ORGANISM: Mus sp.

<400> SEQUENCE: 9

Tyr Leu Asn Gly Asp Gly
 1               5

<210> SEQ ID NO 10
<211> LENGTH: 6
<212> TYPE: PRT
<213> ORGANISM: Mus sp.

<400> SEQUENCE: 10

Asp Asp Thr Ile Phe Ile
 1               5

<210> SEQ ID NO 11
<211> LENGTH: 6
<212> TYPE: PRT
```

```
<213> ORGANISM: Mus sp.

<400> SEQUENCE: 11

Asp Asp Ala Met Phe Leu
 1               5

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
atcagggact ttccgctggg gactt                                      25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
cggaaagtcc ccagcggaaa agtccc                                     26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (14)
<223> OTHER INFORMATION: a, t, c, or g
<221> NAME/KEY: modified_base
<222> LOCATION: (20)
<223> OTHER INFORMATION: a, t, c, or g

<400> SEQUENCE: 14
cggaattcta yytnaayggn gaygg                                      25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (14)
<223> OTHER INFORMATION: a, t, c, or g
<221> NAME/KEY: modified_base
<222> LOCATION: (17)
<223> OTHER INFORMATION: a, t, c, or g

<400> SEQUENCE: 15
cggaattcad raanatngyr tcrtc                                      25

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 16
atttgatgta cccataggat gttccagatt acgctgattt cc                   42
```